United States Patent
Spratt et al.

(10) Patent No.: US 10,786,284 B2
(45) Date of Patent: *Sep. 29, 2020

(54) BONE ANCHOR ASSEMBLIES

(71) Applicant: MEDOS INTERNATIONAL SARL, Le Locle (CH)

(72) Inventors: Frank Spratt, Middleboro, MA (US); Ernest Quintanilha, Norton, MA (US); Thibault Chandanson, Villers le lac (FR)

(73) Assignee: Medos International Sarl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/277,889

(22) Filed: Feb. 15, 2019

(65) Prior Publication Data

US 2019/0209213 A1     Jul. 11, 2019

Related U.S. Application Data

(63) Continuation of application No. 15/692,166, filed on Aug. 31, 2017, now Pat. No. 10,226,282, which is a
(Continued)

(51) Int. Cl.
*A61B 17/70*     (2006.01)

(52) U.S. Cl.
CPC ...... *A61B 17/7035* (2013.01); *A61B 17/7032* (2013.01); *A61B 17/7037* (2013.01)

(58) Field of Classification Search
CPC ............ A61B 17/7032; A61B 17/7034; A61B 17/7035; A61B 17/7037; A61B 17/738
See application file for complete search history.

(56) References Cited

U.S. PATENT DOCUMENTS

| | | | |
|---|---|---|---|
| 2,509,081 A | 5/1950 | Bluth et al. |
| 2,788,045 A | 4/1957 | Rosan |
| | (Continued) | | |

FOREIGN PATENT DOCUMENTS

| | | |
|---|---|---|
| DE | 299 03 342 U1 | 6/1999 |
| EP | 0 470 660 B1 | 7/1995 |
| | (Continued) | |

OTHER PUBLICATIONS

[No Author Listed] A New Angle on Correction. Expedium. DePuy. 2009. 2 pages.
(Continued)

*Primary Examiner* — Julianna N Harvey
(74) *Attorney, Agent, or Firm* — Nutter McClennen & Fish LLP

(57) ABSTRACT

A bone anchor assembly includes a bone anchor, a receiver member for receiving a spinal fixation element to be coupled to the bone anchor, a compression member positioned within the receiver member, and a closure mechanism including an outer set screw and an inner set screw. The outer set screw delivers a distal force to the compression member to fix the bone anchor relative to the receiver member. The proximal surface of the compression member has a shape configured to restrict deformation of the compression member arms including motion of the compression member arms relative to each other. The distal surface of the outer set screw has a shape that is complementary to the shape of the proximal surface of the compression member.

19 Claims, 23 Drawing Sheets

Related U.S. Application Data continuation of application No. 14/029,005, filed on Sep. 17, 2013, now Pat. No. 9,782,204.

(60) Provisional application No. 61/707,062, filed on Sep. 28, 2012.

(56) References Cited

U.S. PATENT DOCUMENTS

| | | |
|---|---|---|
| 2,842,180 A | 7/1958 | Brown et al. |
| 4,124,318 A | 11/1978 | Sagady |
| 4,762,024 A | 8/1988 | Graft |
| 5,009,017 A | 4/1991 | Diekevers et al. |
| 5,129,388 A | 7/1992 | Vignaud et al. |
| 5,154,719 A | 10/1992 | Cotrel |
| 5,306,275 A | 4/1994 | Bryan |
| 5,360,431 A | 11/1994 | Puno et al. |
| 5,385,565 A | 1/1995 | Ray |
| 5,443,467 A | 8/1995 | Biedermann et al. |
| 5,474,555 A | 12/1995 | Puno et al. |
| 5,486,174 A | 1/1996 | Fournet-Fayard et al. |
| 5,487,744 A | 1/1996 | Howland |
| 5,501,684 A | 3/1996 | Schlapfer et al. |
| 5,520,689 A | 5/1996 | Schlapfer et al. |
| 5,562,661 A | 10/1996 | Yoshimi et al. |
| 5,580,246 A | 12/1996 | Fried et al. |
| 5,643,260 A | 7/1997 | Doherty |
| 5,672,176 A | 9/1997 | Biedermann et al. |
| 5,782,833 A | 7/1998 | Haider |
| 5,797,911 A | 8/1998 | Sherman et al. |
| 5,879,350 A | 3/1999 | Sherman et al. |
| 5,885,286 A | 3/1999 | Sherman et al. |
| 5,941,882 A | 8/1999 | Jammet et al. |
| 5,964,591 A | 10/1999 | Beaty et al. |
| 5,989,250 A | 11/1999 | Wagner et al. |
| 6,050,997 A | 4/2000 | Mullane |
| 6,053,917 A | 4/2000 | Sherman et al. |
| 6,056,753 A | 5/2000 | Jackson |
| 6,068,632 A | 5/2000 | Carchidi et al. |
| 6,074,391 A | 6/2000 | Metz-Stavenhagen et al. |
| 6,077,262 A | 6/2000 | Schlapfer et al. |
| 6,090,111 A | 7/2000 | Nichols |
| 6,113,601 A | 9/2000 | Tatar |
| 6,146,383 A | 11/2000 | Studer et al. |
| 6,224,596 B1 | 5/2001 | Jackson |
| 6,224,598 B1 | 5/2001 | Jackson |
| 6,251,112 B1 | 6/2001 | Jackson |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,296,642 B1 | 10/2001 | Morrison et al. |
| 6,302,888 B1 | 10/2001 | Mellinger et al. |
| 6,355,038 B1 | 3/2002 | Pisharodi |
| 6,361,535 B2 | 3/2002 | Jackson |
| 6,379,356 B1 | 4/2002 | Jackson |
| 6,402,757 B1 | 6/2002 | Moore, III et al. |
| 6,440,132 B1 | 8/2002 | Jackson |
| 6,454,768 B1 | 9/2002 | Jackson |
| 6,454,772 B1 | 9/2002 | Jackson |
| 6,458,132 B2 | 10/2002 | Choi |
| 6,475,218 B2 | 11/2002 | Gournay et al. |
| 6,485,491 B1 | 11/2002 | Farris et al. |
| 6,485,494 B1 | 11/2002 | Haider |
| 6,488,681 B2 | 12/2002 | Martin et al. |
| 6,537,276 B2 | 3/2003 | Metz-Stavenhagen |
| 6,540,748 B2 | 4/2003 | Lombardo |
| 6,565,567 B1 | 5/2003 | Haider |
| 6,629,977 B1 | 10/2003 | Wolf |
| 6,660,004 B2 | 12/2003 | Barker et al. |
| 6,663,656 B2 | 12/2003 | Schmieding et al. |
| 6,723,100 B2 | 4/2004 | Biedermann et al. |
| 6,726,480 B1 | 4/2004 | Sutter |
| 6,726,687 B2 | 4/2004 | Jackson |
| 6,730,089 B2 | 5/2004 | Jackson |
| 6,736,820 B2 | 5/2004 | Biedermann et al. |
| 6,740,086 B2 | 5/2004 | Richelsoph |
| 6,755,836 B1 | 6/2004 | Lewis |
| 6,835,196 B2 | 12/2004 | Biedermann et al. |
| 6,843,790 B2 | 1/2005 | Ferree |
| 6,869,433 B2 | 3/2005 | Glascott |
| 6,884,244 B1 | 4/2005 | Jackson |
| 6,974,460 B2 | 12/2005 | Carbone et al. |
| 6,981,973 B2 | 1/2006 | McKinley |
| 6,997,927 B2 | 2/2006 | Jackson |
| 7,018,378 B2 | 3/2006 | Biedermann et al. |
| 7,022,122 B2 | 4/2006 | Amrein et al. |
| 7,083,621 B2 | 8/2006 | Shaolian et al. |
| 7,087,057 B2 | 8/2006 | Konieczynski et al. |
| 7,179,261 B2 | 2/2007 | Sicvol et al. |
| 7,186,255 B2 | 3/2007 | Baynham et al. |
| 7,198,625 B1 | 4/2007 | Hui et al. |
| 7,211,086 B2 | 5/2007 | Biedermann et al. |
| 7,223,268 B2 | 5/2007 | Biedermann |
| 7,235,075 B1 | 6/2007 | Metz-Stavenhagen |
| 7,261,716 B2 | 8/2007 | Strobel et al. |
| 7,264,621 B2 | 9/2007 | Coates et al. |
| 7,291,153 B2 | 11/2007 | Glascott |
| 7,322,981 B2 | 1/2008 | Jackson |
| 7,325,470 B2 | 2/2008 | Kay et al. |
| 7,445,627 B2 | 11/2008 | Hawkes et al. |
| 7,473,267 B2 | 1/2009 | Nguyen et al. |
| 7,559,943 B2 | 7/2009 | Mujwid |
| 7,572,279 B2 | 8/2009 | Jackson |
| 7,591,839 B2 | 9/2009 | Biedermann et al. |
| 7,604,655 B2 | 10/2009 | Warnick |
| 7,615,068 B2 | 11/2009 | Timm et al. |
| 7,625,394 B2 | 12/2009 | Molz, IV et al. |
| 7,670,362 B2 | 3/2010 | Zergiebel |
| 7,674,277 B2 | 3/2010 | Burd et al. |
| 7,678,137 B2 | 3/2010 | Butler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,699,876 B2 | 4/2010 | Barry et al. |
| 7,717,942 B2 | 5/2010 | Schumacher |
| 7,722,649 B2 | 5/2010 | Biedermann et al. |
| 7,727,261 B2 | 6/2010 | Barker et al. |
| 7,731,736 B2 | 6/2010 | Guenther et al. |
| 7,736,380 B2 | 6/2010 | Johnston et al. |
| 7,766,946 B2 | 8/2010 | Bailly |
| 7,785,354 B2 | 8/2010 | Biedermann et al. |
| 7,789,900 B2 | 9/2010 | Levy et al. |
| 7,846,190 B2 | 12/2010 | Ball |
| 7,850,718 B2 | 12/2010 | Bette et al. |
| 7,857,834 B2 | 12/2010 | Boschert |
| 7,867,257 B2 | 1/2011 | Na et al. |
| 7,892,259 B2 | 2/2011 | Biedermann et al. |
| 7,901,413 B1 | 3/2011 | Lewis |
| 7,922,748 B2 | 4/2011 | Hoffman |
| 7,951,173 B2 | 5/2011 | Hammill, Sr. et al. |
| 7,951,175 B2 | 5/2011 | Chao et al. |
| 7,955,363 B2 | 6/2011 | Richelsoph |
| 8,007,522 B2 | 8/2011 | Hutchinson |
| 8,016,862 B2 | 9/2011 | Felix et al. |
| 8,052,724 B2 | 11/2011 | Jackson |
| 8,057,518 B2 | 11/2011 | Frasier et al. |
| 8,066,744 B2 | 11/2011 | Justis et al. |
| 8,066,745 B2 | 11/2011 | Kirschman |
| 8,075,599 B2 | 12/2011 | Johnson et al. |
| 8,083,774 B2 | 12/2011 | Teitelbaum |
| 8,092,494 B2 | 1/2012 | Butler et al. |
| 8,097,023 B2 | 1/2012 | Cline, Jr. et al. |
| 8,097,025 B2 | 1/2012 | Hawkes et al. |
| 8,100,946 B2 | 1/2012 | Strausbaugh et al. |
| 8,114,134 B2 | 2/2012 | Winslow et al. |
| 8,162,989 B2 | 4/2012 | Khalili |
| 8,167,910 B2 | 5/2012 | Nilsson |
| 8,167,912 B2 | 5/2012 | Jacofsky et al. |
| 8,197,517 B1 | 6/2012 | Lab et al. |
| 8,197,518 B2 | 6/2012 | Hammill, Sr. et al. |
| 8,221,471 B2 | 7/2012 | Kovach et al. |
| 8,221,472 B2 | 7/2012 | Peterson et al. |
| 8,236,035 B1 | 8/2012 | Bedor |
| 8,241,341 B2 | 8/2012 | Walker et al. |
| 8,257,396 B2 | 9/2012 | Jackson |

(56) References Cited

U.S. PATENT DOCUMENTS

| | | |
|---|---|---|
| 8,257,399 B2 | 9/2012 | Biedermann et al. |
| 8,267,968 B2 | 9/2012 | Remington et al. |
| 8,273,112 B2 | 9/2012 | Garamszegi et al. |
| 8,277,490 B2 | 10/2012 | Freeman et al. |
| 8,287,576 B2 | 10/2012 | Barrus |
| 8,298,270 B2 | 10/2012 | Justis et al. |
| 8,298,274 B2 | 10/2012 | Barker, Jr. et al. |
| 8,303,594 B2 | 11/2012 | Lynch et al. |
| 8,308,782 B2 | 11/2012 | Jackson |
| 8,313,515 B2 | 11/2012 | Brennan et al. |
| 8,313,516 B2 | 11/2012 | Konieczynski et al. |
| 8,337,530 B2 | 12/2012 | Hestad et al. |
| 8,343,191 B2 | 1/2013 | Matthis et al. |
| 8,377,100 B2 | 2/2013 | Jackson |
| 8,409,260 B2 | 4/2013 | Biedermann et al. |
| 8,430,914 B2 | 4/2013 | Spratt et al. |
| 8,465,528 B2 | 6/2013 | Schumacher |
| 8,465,530 B2 | 6/2013 | Hammill, Sr. et al. |
| 8,491,640 B1 | 7/2013 | Robinson |
| 8,491,641 B2 | 7/2013 | Nihalani |
| 8,556,938 B2 | 10/2013 | Jackson et al. |
| 8,556,941 B2 | 10/2013 | Hutchinson |
| 8,608,746 B2 | 12/2013 | Kolb et al. |
| 8,951,294 B2 | 2/2015 | Gennari et al. |
| 9,155,580 B2 | 10/2015 | Cormier et al. |
| 9,216,041 B2 * | 12/2015 | Jackson ............. A61B 17/7004 |
| 9,259,247 B2 | 2/2016 | Chandanson et al. |
| 9,402,673 B2 | 8/2016 | Cormier et al. |
| 9,433,445 B2 | 9/2016 | Ramsay et al. |
| 9,662,143 B2 | 5/2017 | Jackson |
| RE46,431 E | 6/2017 | Jackson |
| 9,700,354 B2 | 7/2017 | Jackson |
| 9,713,488 B2 | 7/2017 | Hutchinson |
| 9,724,130 B2 | 8/2017 | Chandanson et al. |
| 9,724,145 B2 | 8/2017 | Spratt et al. |
| 9,775,660 B2 | 10/2017 | Spratt et al. |
| 9,782,204 B2 | 10/2017 | Spratt et al. |
| 9,788,866 B2 | 10/2017 | Jackson |
| 9,801,665 B2 | 10/2017 | Jackson |
| 9,918,747 B2 | 3/2018 | Spratt et al. |
| 10,058,354 B2 | 8/2018 | Jackson et al. |
| 10,201,377 B2 | 2/2019 | Hutchinson |
| 10,226,282 B2 * | 3/2019 | Spratt ................ A61B 17/7035 |
| 10,321,938 B2 | 6/2019 | Chandanson et al. |
| 10,342,582 B2 | 7/2019 | Spratt et al. |
| 10,413,342 B2 | 9/2019 | Spratt et al. |
| 2002/0026193 A1 | 2/2002 | Barker et al. |
| 2002/0058942 A1 | 5/2002 | Biedermann et al. |
| 2002/0133159 A1 | 9/2002 | Jackson |
| 2003/0023243 A1 * | 1/2003 | Biedermann ...... A61B 17/7032 606/308 |
| 2003/0055426 A1 | 3/2003 | Carbone et al. |
| 2003/0073996 A1 | 4/2003 | Doubler et al. |
| 2003/0100896 A1 * | 5/2003 | Biedermann ...... A61B 17/7032 606/305 |
| 2003/0100904 A1 * | 5/2003 | Biedermann ...... A61B 17/7032 606/272 |
| 2003/0125741 A1 * | 7/2003 | Biedermann ...... A61B 17/7032 606/278 |
| 2003/0153911 A1 | 8/2003 | Shluzas |
| 2004/0049190 A1 | 3/2004 | Biedermann et al. |
| 2004/0116929 A1 | 6/2004 | Barker et al. |
| 2004/0153077 A1 | 8/2004 | Biedermann et al. |
| 2004/0162560 A1 | 8/2004 | Raynor et al. |
| 2004/0186473 A1 | 9/2004 | Cournoyer et al. |
| 2004/0186478 A1 | 9/2004 | Jackson |
| 2004/0193160 A1 | 9/2004 | Richelsoph |
| 2004/0243126 A1 | 12/2004 | Carbone et al. |
| 2005/0055026 A1 | 3/2005 | Biedermann et al. |
| 2005/0080415 A1 | 4/2005 | Keyer et al. |
| 2005/0153077 A1 | 7/2005 | Gedeon et al. |
| 2005/0154391 A1 | 7/2005 | Doherty et al. |
| 2005/0154393 A1 | 7/2005 | Doherty et al. |
| 2005/0159750 A1 | 7/2005 | Doherty |
| 2005/0182401 A1 | 8/2005 | Timm et al. |
| 2005/0187548 A1 | 8/2005 | Butler et al. |
| 2005/0216003 A1 | 9/2005 | Biedermann et al. |
| 2005/0228326 A1 | 10/2005 | Kalfas et al. |
| 2005/0273101 A1 | 12/2005 | Schumacher |
| 2005/0277928 A1 | 12/2005 | Boschert |
| 2006/0025771 A1 | 2/2006 | Jackson |
| 2006/0083603 A1 | 4/2006 | Jackson |
| 2006/0084995 A1 | 4/2006 | Biedermann et al. |
| 2006/0100621 A1 | 5/2006 | Jackson |
| 2006/0100622 A1 | 5/2006 | Jackson |
| 2006/0106383 A1 | 5/2006 | Biedermann et al. |
| 2006/0149241 A1 | 7/2006 | Richelsoph et al. |
| 2006/0161153 A1 | 7/2006 | Hawkes et al. |
| 2006/0200128 A1 | 9/2006 | Mueller |
| 2006/0241599 A1 | 10/2006 | Konieczynski et al. |
| 2006/0264933 A1 | 11/2006 | Baker et al. |
| 2007/0055244 A1 | 3/2007 | Jackson |
| 2007/0118117 A1 | 5/2007 | Altarac et al. |
| 2007/0118123 A1 | 5/2007 | Strausbaugh et al. |
| 2007/0123862 A1 | 5/2007 | Warnick |
| 2007/0123870 A1 | 5/2007 | Jeon et al. |
| 2007/0233078 A1 | 10/2007 | Justis et al. |
| 2007/0260246 A1 | 11/2007 | Biedermann |
| 2007/0265621 A1 | 11/2007 | Matthis et al. |
| 2007/0270813 A1 | 11/2007 | Garamszegi |
| 2007/0293862 A1 | 12/2007 | Jackson |
| 2008/0021473 A1 | 1/2008 | Butler et al. |
| 2008/0045953 A1 | 2/2008 | Garamszegi |
| 2008/0119852 A1 | 5/2008 | Dalton et al. |
| 2008/0132957 A1 | 6/2008 | Matthis et al. |
| 2008/0147129 A1 | 6/2008 | Biedermann et al. |
| 2008/0161859 A1 | 7/2008 | Nilsson |
| 2008/0200956 A1 | 8/2008 | Beckwith et al. |
| 2008/0215100 A1 | 9/2008 | Matthis et al. |
| 2008/0269805 A1 | 10/2008 | Dekutoski et al. |
| 2008/0269809 A1 | 10/2008 | Garamszegi |
| 2008/0288001 A1 | 11/2008 | Cawley et al. |
| 2008/0294202 A1 | 11/2008 | Peterson et al. |
| 2008/0312692 A1 | 12/2008 | Brennan et al. |
| 2009/0005813 A1 | 1/2009 | Crall et al. |
| 2009/0012567 A1 | 1/2009 | Biedermann et al. |
| 2009/0018591 A1 | 1/2009 | Hawkes et al. |
| 2009/0062861 A1 | 3/2009 | Frasier et al. |
| 2009/0118772 A1 | 5/2009 | Diederich et al. |
| 2009/0163962 A1 | 6/2009 | Dauster et al. |
| 2009/0182384 A1 | 7/2009 | Wilcox et al. |
| 2009/0198280 A1 | 8/2009 | Spratt et al. |
| 2009/0216280 A1 * | 8/2009 | Hutchinson ............ A61B 17/88 606/279 |
| 2009/0228051 A1 | 9/2009 | Kolb et al. |
| 2009/0228053 A1 | 9/2009 | Kolb et al. |
| 2009/0254125 A1 | 10/2009 | Predick |
| 2009/0264896 A1 | 10/2009 | Biedermann et al. |
| 2009/0264933 A1 | 10/2009 | Carls et al. |
| 2009/0287261 A1 | 11/2009 | Jackson |
| 2009/0326587 A1 | 12/2009 | Matthis et al. |
| 2010/0004693 A1 | 1/2010 | Miller et al. |
| 2010/0010547 A1 | 1/2010 | Beaurain et al. |
| 2010/0020272 A1 | 1/2010 | Kim et al. |
| 2010/0023061 A1 | 1/2010 | Randol et al. |
| 2010/0030272 A1 | 2/2010 | Winslow et al. |
| 2010/0103099 A1 | 4/2010 | Lee |
| 2010/0114174 A1 | 5/2010 | Jones et al. |
| 2010/0152785 A1 | 6/2010 | Forton et al. |
| 2010/0160977 A1 | 6/2010 | Gephart et al. |
| 2010/0168747 A1 | 7/2010 | Lynch et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222827 A1 | 9/2010 | Griffiths et al. |
| 2010/0234891 A1 | 9/2010 | Freeman et al. |
| 2010/0305621 A1 | 12/2010 | Wang et al. |
| 2010/0312279 A1 | 12/2010 | Gephart et al. |
| 2011/0046683 A1 * | 2/2011 | Biedermann ...... A61B 17/7035 606/305 |
| 2011/0106179 A1 | 5/2011 | Prevost et al. |
| 2011/0160778 A1 | 6/2011 | Elsbury |
| 2011/0160779 A1 | 6/2011 | Schlaepfer et al. |
| 2011/0190822 A1 | 8/2011 | Spitler et al. |

(56) References Cited

U.S. PATENT DOCUMENTS

| | | |
|---|---|---|
| 2011/0213424 A1 | 9/2011 | Biedermann et al. |
| 2011/0245876 A1 | 10/2011 | Brumfield |
| 2011/0245877 A1 | 10/2011 | Pisharodi |
| 2011/0251650 A1 | 10/2011 | Biedermann et al. |
| 2011/0270322 A1 | 11/2011 | Olsen et al. |
| 2011/0276098 A1 | 11/2011 | Biedermann et al. |
| 2011/0282399 A1 | 11/2011 | Jackson |
| 2011/0288592 A1 | 11/2011 | McKinley |
| 2011/0288599 A1 | 11/2011 | Michielli et al. |
| 2011/0295321 A1 | 12/2011 | Hutchinson |
| 2012/0010661 A1 | 1/2012 | Farris et al. |
| 2012/0022593 A1 | 1/2012 | Kovach et al. |
| 2012/0035670 A1 | 2/2012 | Jackson et al. |
| 2012/0046701 A1 | 2/2012 | Gennari et al. |
| 2012/0059425 A1 | 3/2012 | Biedermann |
| 2012/0059426 A1 | 3/2012 | Jackson et al. |
| 2012/0078307 A1 | 3/2012 | Nihalani |
| 2012/0083845 A1 | 4/2012 | Winslow et al. |
| 2012/0089194 A1 | 4/2012 | Strausbaugh et al. |
| 2012/0136395 A1 | 5/2012 | Biedermann et al. |
| 2012/0143266 A1 | 6/2012 | Jackson et al. |
| 2012/0150239 A1 | 6/2012 | Garamszegi |
| 2012/0165881 A1 | 6/2012 | Biedermann et al. |
| 2012/0165882 A1 | 6/2012 | Biedermann et al. |
| 2012/0179209 A1 | 7/2012 | Biedermann et al. |
| 2012/0185003 A1 | 7/2012 | Biedermann et al. |
| 2012/0197313 A1 | 8/2012 | Cowan |
| 2012/0209336 A1 | 8/2012 | Jackson et al. |
| 2012/0253404 A1 | 10/2012 | Timm et al. |
| 2012/0277805 A1 | 11/2012 | Farris |
| 2012/0303070 A1 | 11/2012 | Jackson |
| 2012/0310290 A1 | 12/2012 | Jackson |
| 2012/0316605 A1 | 12/2012 | Palagi |
| 2012/0328394 A1 | 12/2012 | Biedermann et al. |
| 2012/0330364 A1 | 12/2012 | Jacofsky et al. |
| 2013/0013003 A1 | 1/2013 | Carbone et al. |
| 2013/0046350 A1 | 2/2013 | Jackson et al. |
| 2013/0053901 A1 | 2/2013 | Cormier et al. |
| 2013/0096618 A1 | 4/2013 | Chandanson et al. |
| 2013/0096623 A1 | 4/2013 | Biedermann et al. |
| 2013/0103093 A1 | 4/2013 | Biedermann et al. |
| 2013/0110172 A1 | 5/2013 | Biedermann et al. |
| 2013/0110180 A1 | 5/2013 | Doubler et al. |
| 2013/0144346 A1 | 6/2013 | Jackson et al. |
| 2013/0150904 A1* | 6/2013 | Biedermann ........ A61B 17/84 606/328 |
| 2013/0211467 A1 | 8/2013 | Dickinson |
| 2014/0018861 A1 | 1/2014 | Hutchinson |
| 2014/0025119 A1 | 1/2014 | Biedermann et al. |
| 2014/0094849 A1 | 4/2014 | Spratt et al. |
| 2014/0142633 A1 | 5/2014 | Jackson et al. |
| 2014/0142634 A1* | 5/2014 | Schlaepfer ........ A61B 17/704 606/278 |
| 2014/0277153 A1 | 9/2014 | Spratt et al. |
| 2014/0277157 A1 | 9/2014 | Chandanson et al. |
| 2014/0277158 A1 | 9/2014 | Spratt et al. |
| 2014/0277159 A1 | 9/2014 | Spratt et al. |
| 2014/0277161 A1 | 9/2014 | Spratt et al. |
| 2014/0277162 A1 | 9/2014 | Kostuik et al. |
| 2014/0277189 A1 | 9/2014 | Spratt et al. |
| 2015/0173816 A1 | 6/2015 | Biedermann et al. |
| 2016/0128733 A1 | 5/2016 | Spratt et al. |
| 2016/0135848 A1 | 5/2016 | Chandanson et al. |
| 2017/0296235 A1 | 10/2017 | Chandanson et al. |
| 2017/0354446 A1 | 12/2017 | Spratt et al. |
| 2017/0354448 A1 | 12/2017 | Hutchinson |
| 2017/0360482 A1 | 12/2017 | Spratt et al. |
| 2017/0360491 A1 | 12/2017 | Spratt et al. |
| 2019/0239936 A1 | 8/2019 | Hutchinson |
| 2019/0254717 A1 | 8/2019 | Chandanson et al. |
| 2019/0365426 A1 | 12/2019 | Spratt et al. |

FOREIGN PATENT DOCUMENTS

| | | |
|---|---|---|
| EP | 1 295 566 A1 | 3/2003 |
| EP | 0 857 465 B1 | 6/2003 |
| EP | 1 570 794 A1 | 9/2005 |
| EP | 1 774 919 B1 | 8/2008 |
| EP | 1 795 134 B1 | 8/2008 |
| EP | 2 070 485 A1 | 6/2009 |
| EP | 1 694 229 B1 | 7/2010 |
| EP | 2 272 451 A1 | 1/2011 |
| EP | 2 286 748 A1 | 2/2011 |
| EP | 2 455 028 A1 | 5/2012 |
| EP | 2 129 310 B1 | 9/2012 |
| WO | 91/016020 A1 | 10/1991 |
| WO | 2004/058081 A1 | 7/2004 |
| WO | 2008/024937 A2 | 2/2008 |
| WO | 2008/119006 A1 | 10/2008 |
| WO | 2009/073655 A1 | 6/2009 |
| WO | 2010/056846 A2 | 5/2010 |
| WO | 2011/059732 A1 | 5/2011 |
| WO | 2011/109009 A1 | 9/2011 |
| WO | 2011/127065 A1 | 10/2011 |
| WO | 2012/024665 A2 | 2/2012 |
| WO | 2012/030712 A1 | 3/2012 |
| WO | 2012/035479 A2 | 3/2012 |
| WO | 2012/060868 A1 | 5/2012 |
| WO | 2013/028851 A1 | 2/2013 |

OTHER PUBLICATIONS

[No Author Listed] Definition of "clip," www.thefreedictionary.com/clip; accessed May 16, 2015.

[No Author Listed] Expedium Spine System, Dual Innie Independent Locking Technology Brochure, DePuy Spine, Aug. 1, 2004, 6 pages.

[No Author Listed] Moss Miami Polyaxial Reduction Screw Surgical Technique, DePuy AcroMed, Inc. 1998.

[No Author Listed] Straight Talk with Expedium. Expedium. 10 pages. Jul. 2007.

[No Author Listed] Surgical Technique Guide and Ordering Information. Expedium. DePuy Spine Inc. Sep. 2011. 24 Pages.

[No Author Listed] Value Analysis Brief—Expedium Favored Angle Screw. DePuy Synthes Spine. Aug. 2012. 4 pages.

[No Author Listed] Viper 2 MIS Extended Tab , DePuy Spine, Inc., Feb. 1, 2009.

[No Author Listed] Viper 2 MIS Spine System, System Guide. DePuy Spine Inc. Sep. 2011. 60 pages.

Duerig, T. W., et al., "An Engineer's Perspective of Pseudoelasticity," p. 370, in Engineering Aspects of Shape Memory Alloys, Butterworth-Heinemann, 1990.

International Search Report and Written Opinion for Application No. PCT/US2013/060350, dated Jan. 3, 2014 (9 pages).

International Search Report for PCT/US14/021198 dated Jun. 5, 2014 (3 Pages).

International Preliminary Report on Patentability for Application No. PCT/US2014/021198, dated Sep. 24, 2015 (7 pages).

U.S. Appl. No. 61/706,860, filed Sep. 28, 2012 (66 pages).

* cited by examiner

BONE ANCHOR ASSEMBLIES

CROSS REFERENCE TO RELATED APPLICATIONS

This application is a continuation of U.S. application Ser. No. 15/692,166, filed on Aug. 31, 2017. U.S. application Ser. No. 15/692,166 is a continuation of U.S. application Ser. No. 14/029,005, filed Sep. 17, 2013 and now issued as U.S. Pat. No. 9,782,204. U.S. application Ser. No. 14/029,005 claims priority to U.S. Provisional Patent Application No. 61/707,062, filed Sep. 28, 2012. The entire contents of each of these applications are incorporated herein by reference.

BACKGROUND

Bone anchors may be used in orthopedic surgery to fix bone during the healing or fusion process. In spinal surgery, bone anchors may be used with spinal fixation elements, such as spinal rods, to stabilize multiple vertebrae either rigidly, in which no relative motion between the vertebrae is desired, and dynamically, in which limited, controlled motion between the vertebrae is desired. A closure mechanism is typically used to secure the spinal fixation element between two spaced apart arms of the receiver member of the bone anchor. In certain bone anchor assemblies, the spinal fixation element is also positioned between the spaced apart arms of a compression member positioned within the receiver member. Tightening of the closure mechanism can cause deformation of the components of the bone anchor assembly including, for example, the receiver member or the compression member. Such deformation can cause the arms of the receiver mechanism or the arms of the compression member to separate or splay, which can result in the closure mechanism loosening over time and, in the worst case, the spinal fixation element separating from the bone anchor assembly.

Accordingly, there is a need for improved bone anchor assemblies in which deformation of the components of the assembly is minimized during tightening.

SUMMARY

Disclosed herein are improved bone anchor assemblies and, in particular, improved bone anchor assemblies used in connection with spinal fixation elements to fix multiple vertebrae.

In accordance with one aspect, a bone anchor assembly includes a bone anchor having a proximal head and a distal shaft configured to engage bone, a receiver member for receiving a spinal fixation element to be coupled to the bone anchor, a compression member positioned within the central passage of the receiver member, an outer set screw, and an inner set screw.

The receiver member has a proximal end, a distal end, and a central passage. The proximal end of the receiver member has a pair of spaced apart receiver member arms defining a recess therebetween and the receiver member arms may include an inner thread. The distal end of the receiver member has a distal end surface defining opening through which at least a portion of the bone anchor extends. The central passage extends between the proximal end and the distal end and communicates with the opening in the distal end surface. The central passage has a central longitudinal axis extending between the proximal end and the distal end.

The compression member has a proximal end and a distal end. The proximal end of the compression member has a pair of spaced apart compression member arms defining a U-shaped seat for receiving the rod. Each compression member arm has a proximal surface. The distal end of the compression member has a distal surface engageable with the proximal head of the bone anchor.

The outer set screw includes a first outer thread for engaging the first inner thread of the receiver member arms. The outer set screw has a distal surface engageable with the proximal surfaces of the compression member arms and a set screw central passage from a top surface of the outer set screw to a bottom surface of the outer set screw. The set screw central passage has a second internal thread.

The inner set screw is positionable within the set screw central passage and has a second outer thread for engaging the second inner thread of the outer set screw. The inner set screw is operable to act on the spinal rod to fix the spinal rod relative to the receiver member.

Engagement of the outer set screw with the receiver member arms results in the distal surface of the outer set screw engaging the proximal surface of the compression member arms and the outer set screw thereby delivering a distal force to the compression member to fix the bone anchor relative to the receiver member. The proximal surface of the compression member arms has a shape configured to resist deformation of the compression member arms and, in particular, to restrict relative movement of the compression member arms both towards and away from each other. The distal surface of the outer set screw has a shape that is complementary to the shape of the proximal surface of the compression member arms.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

DETAIL DESCRIPTION OF EXEMPLARY EMBODIMENTS

Figure 1:
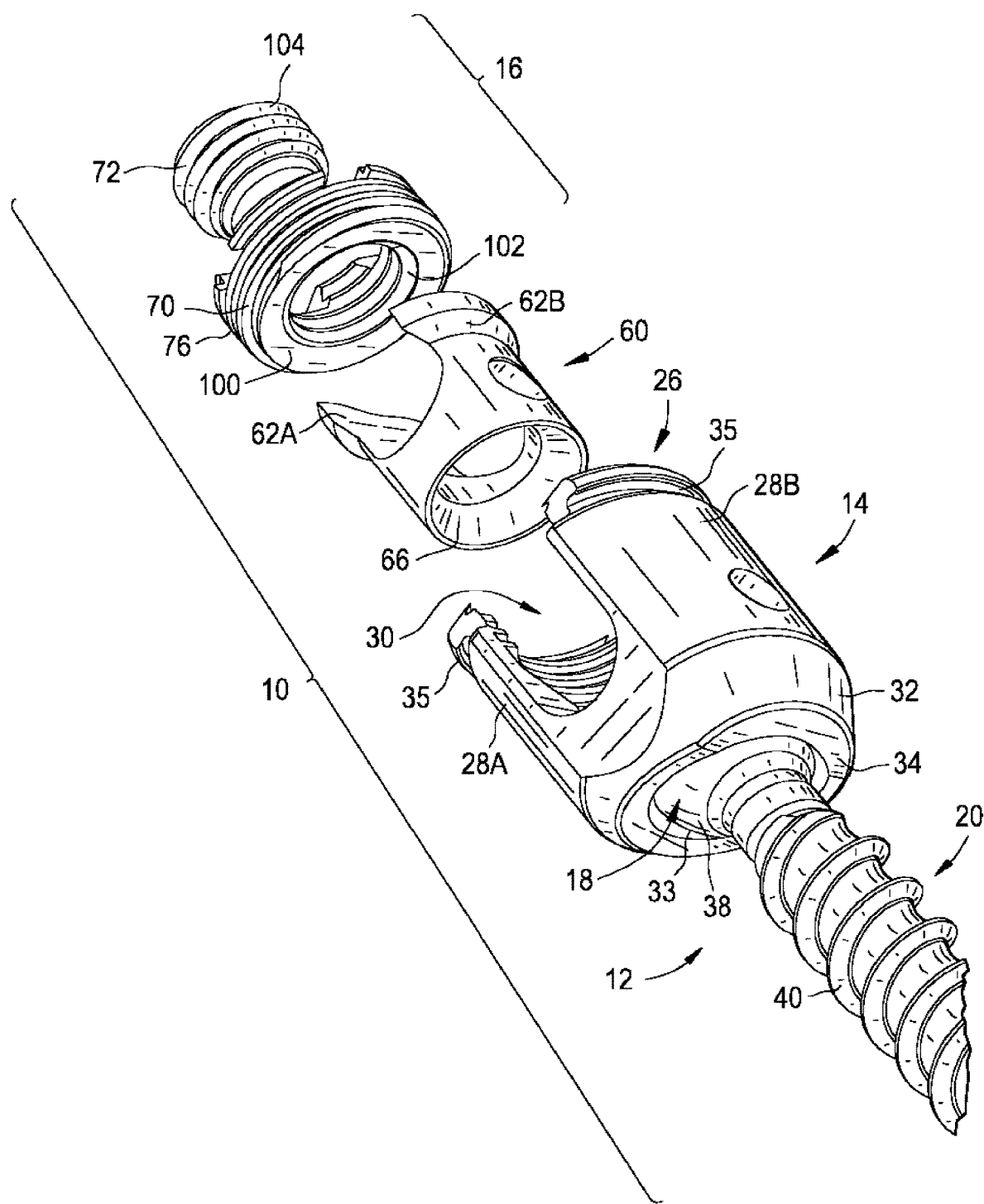
FIG. 1 is an exploded, perspective view of an exemplary embodiment of a bone anchor assembly.
Figure 2:
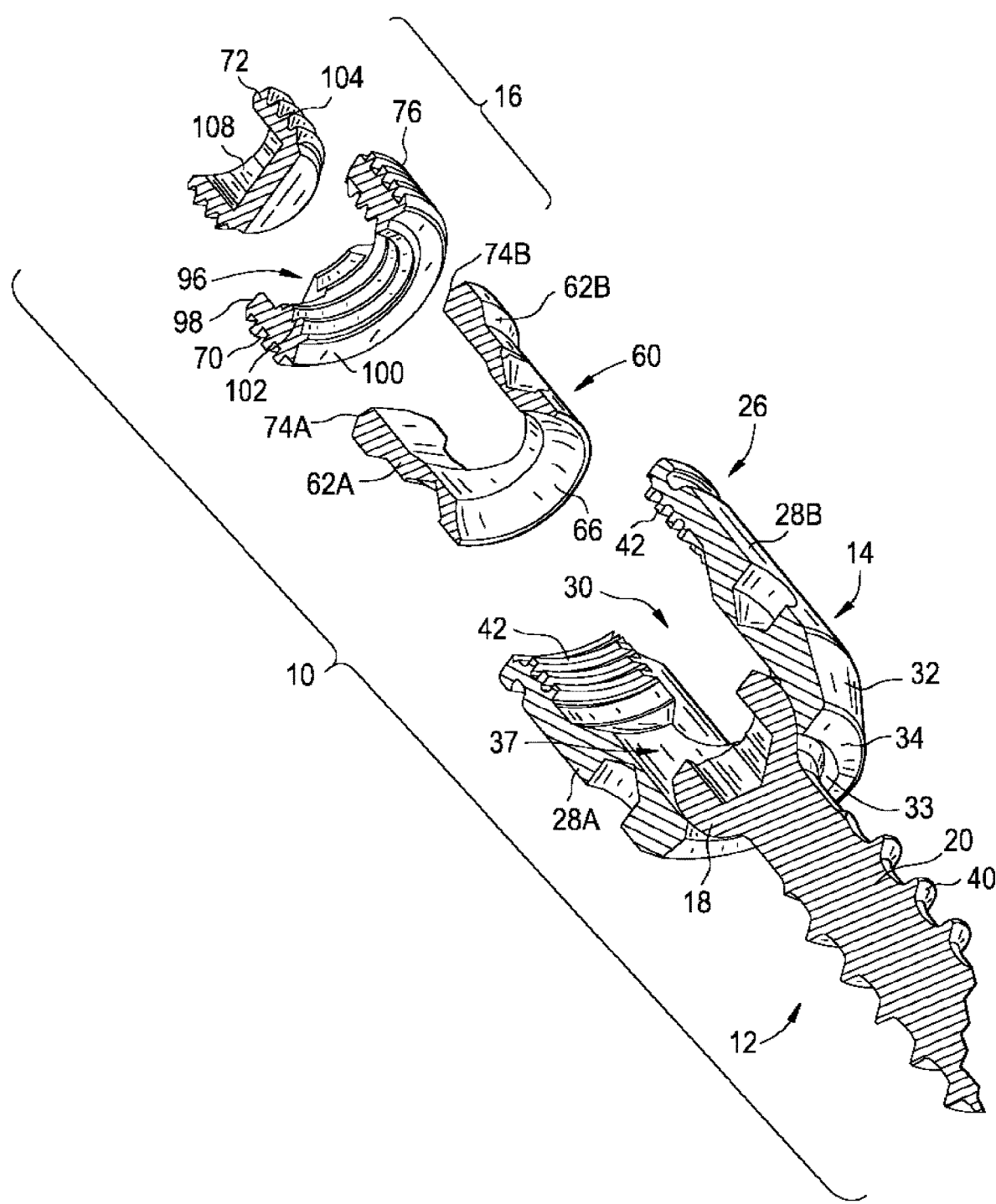
FIG. 2 is an exploded view in cross section of the bone anchor assembly of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-5 illustrate an exemplary embodiment of a bone anchor assembly 10 including a bone anchor 12, a receiver member 14 for receiving a spinal fixation element, such as a spinal rod 22, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart receiver member arms 28A, 28B defining a recess 30 therebetween and a distal end 32 having a distal end surface 34 defining opening 33 through which at least a portion of the bone anchor 12 extends. The closure mechanism 16 may be positionable between and may engage the arms 28A, 28B to capture a spinal fixation element, e.g., spinal rod 22, within the receiver member 14 and fix the spinal fixation element with respect to the receiver member 14.

Continuing to refer to FIGS. 1-5, the proximal head 16 of the bone anchor 12 in the exemplary embodiment is generally in the shape of a truncated sphere having a planar proximal surface 36 and an approximately spherically shaped distal surface 38. The exemplary bone anchor assembly is a polyaxial bone screw designed for posterior implantation in the pedicle or lateral mass of a vertebra. In this regards, the proximal head 18 of the bone anchor 12 engages the distal end 32 of the receiver member 14 in a ball and socket like arrangement in which the proximal head 18, and thus the distal shaft 20, can pivot relative to the receiver member 14. The distal surface 38 of the proximal head 18 of the bone anchor 12 and the mating surface within the distal end 32 of the receiver member 14 may have any shape that facilitates this ball and socket like arrangement, including, for example, spherical (as illustrated), toroidal, conical, frustoconical, and any combinations of these shapes.

The distal shaft 20 of the bone anchor 12 may be configured to engage bone and, in the illustrated embodiment, includes an external bone engaging thread 40. The thread form for the distal shaft 20, including the number of threads, the pitch, major and minor diameter, and thread shape, may be selected to facilitate connection with bone. Examples of exemplary thread forms are disclosed in U.S. Patent Application Publication No. 2011-0288599, filed May 18, 2011, and U.S. Patent Application Publication No. US 2013-0053901, filed Aug. 22, 2012, both of which are incorporated herein by reference. Alternatively, the distal shaft 20 may include other structures for engaging bone, including a hook. The distal shaft 20 of the bone anchor 12 may be cannulated, having a central passage or cannula extending the length of the bone anchor to facilitate delivery of the bone anchor over a guide wire in, for example, minimally invasive procedures. The other components of the bone anchor assembly, including the closure member 16, the receiver member 14, and the compression member 60 (discussed below) may be cannulated or otherwise have an opening to permit the respective component to be delivered over a guide wire. The distal shaft 20 may also include one or more side wall openings or fenestrations that communicate with the cannula to permit bone in-growth or to permit the dispensing of bone cement or other materials through the bone anchor 10. The side wall openings may extend radially from the cannula through the side wall of the distal shaft 20. Exemplary systems for delivering bone cement to the bone anchor assembly 10 and alternative bone anchor configurations for facilitating cement delivery are described in U.S. Patent Application Publication No. 2010/0114174, which is hereby incorporated herein by reference. The distal shaft 20 of the bone anchor 12 may also be coated with materials to permit bone growth, such as, for example, hydroxyl apatite, and the bone anchor assembly 10 may be coated all or in-part with anti-infective materials, such as, for example, tryclosan.

Figure 3:
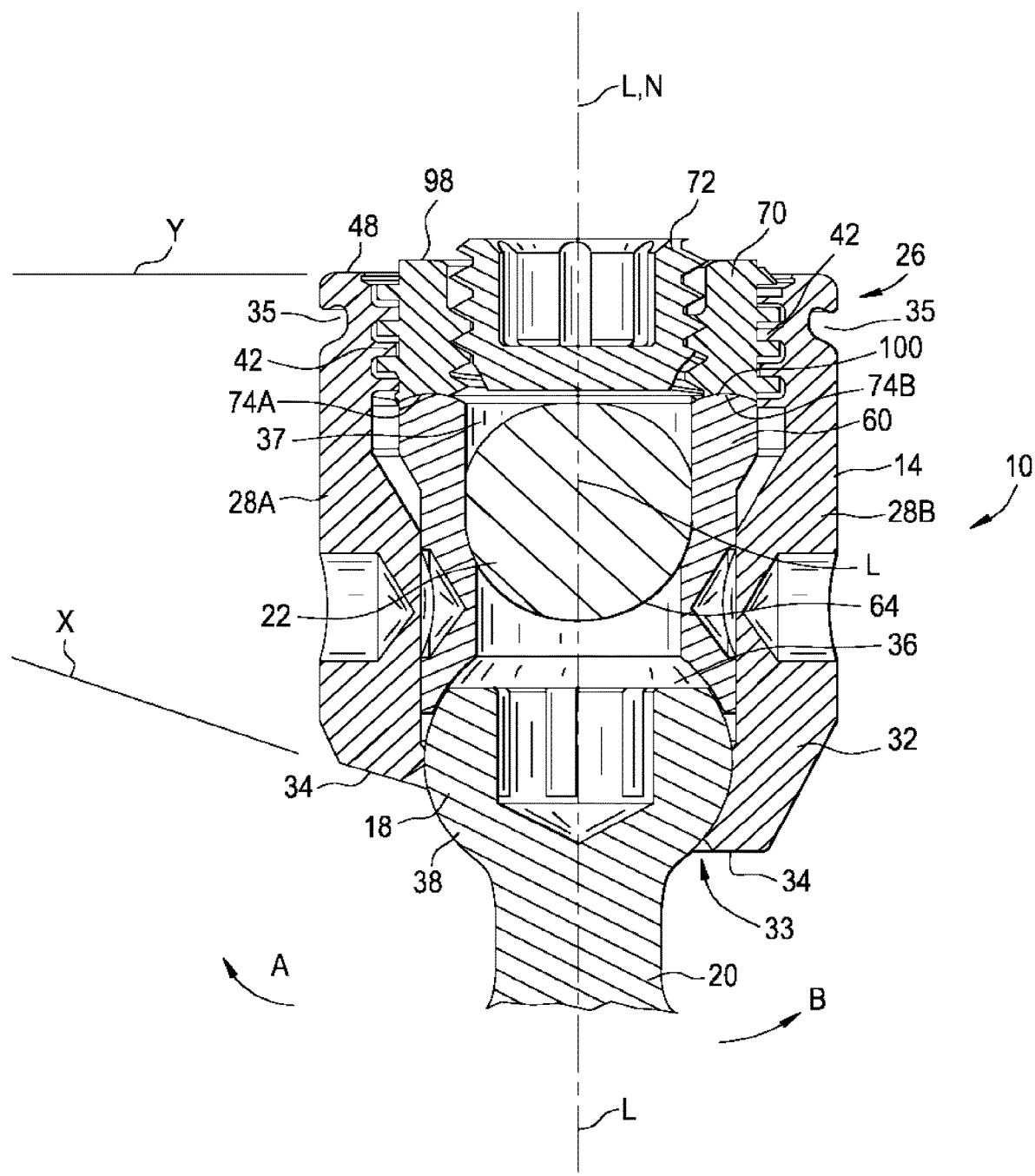
FIG. 3 is a side view in cross section of the bone anchor assembly FIG. 1.

Continuing to refer to FIGS. 1-5, the proximal end 26 of the receiver member 14 of the exemplary bone anchor assembly 10 includes a pair of spaced apart arms 28A, 28B defining the U-shaped recess 30 therebetween for receiving a spinal fixation element. e.g., a spinal rod. Each receiver member arm 28A, 28B of the proximal end 26 of the receiver member 14 extends from the distal end 32 of the receiver member 14 to a free end. The outer surface of each arm 28A, 28B may include a feature, such as a recess, dimple, notch, projection, or the like, to facilitate connection of the receiver member 14 and, thus, the bone anchor assembly 10, to instruments. For example, the outer surface of each arm 28A, 28B may include an arcuate groove 35 at the respective free end of the arms. Such grooves are described in more detail in U.S. Pat. No. 7,179,261, which is incorporated herein by reference. At least a portion of the proximal end surface 48 of the receiver member 12 defines a plane Y, as illustrated in FIG. 3.

The distal end 32 of the receiver member 14 includes a distal end surface 34 which is generally annular in shape defining a circular opening through which at least a portion of the bone anchor 12 extends. For example, the distal shaft 20 of the bone anchor 12 may extend through the opening. At least a portion of the distal end surface 34 defines a plane X.

The receiver member 14 includes a central passage 37 extending between the proximal end 26 and the distal end 32. The central passage 37 communicates with the opening 33 in the distal end surface 34 of the distal end 32 of the receiver member 14. The central passage 37 and the receiver member 14 having a common central longitudinal axis L extending between the proximal end 26 and the distal end 32 of the receiver member 14.

The exemplary bone anchor assembly is a rigid polyaxial screw in which the bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The exemplary bone anchor is a favored-angle polyaxial screw in which the cone of angulation is biased in one direction. In this manner, the bone anchor 12 is movable relative to the receiver member 14 in at least a first direction, indicated by arrow A in FIG. 3 and the bone anchor 12 is also movable in at least a second direction, indicated by arrow B in FIG. 3. The shaft 20 of the bone anchor 12 is movable more in the direction indicated by arrow A than in the direction indicated by arrow B. The distal shaft 20 of the bone anchor 12 defines a neutral axis with respect to the receiver member 14. In the exemplary favored-angle polyaxial screw embodiment, the neutral axis is oriented perpendicular to the plane X defined by the distal end surface 34 and intersects the center point of the opening in the distal end surface 34 through which the distal shaft 20 of the bone anchor 12 extends. The neutral axis is oriented at an angle to the central longitudinal axis L of the receiver member 14 in one exemplary manner of providing biased angulation of the bone anchor 12. In one exemplary manner of providing biased angulation, the plane Y defined by at least a portion of the proximal end surface 48 of the receiver member 14 intersects the plane X defined by at least a portion of the distal end surface 34 of the receiver member 12. In addition (or in the alternative), the proximal end 26 of the receiver member 14 may include a proximal first bore coaxial with a first central longitudinal axis N (which is coincident with longitudinal axis L) and a distal second bore coaxial with a second central longitudinal axis (which is coincident with neutral axis) and the first central longitudinal axis N and second central longitudinal axis can intersect one another. The angle between the plane X and plane Y and the angle between the first central longitudinal axis N and second longitudinal axis can be selected to provide the desired degree of biased angulation. Examples of favored angled polyaxial screws are described in more detail in U.S. Patent Application Publication 2003/0055426 and U.S. Pat. No. 6,736,820, both of which are incorporated herein by reference. In alternative embodiments, the bone anchor assembly can be a conventional (non-biased) polyaxial screw in which the bone anchor pivots in the same amount in every direction and has a neutral axis that is coincident with the central longitudinal axis L of the receiver member.

Figure 4:
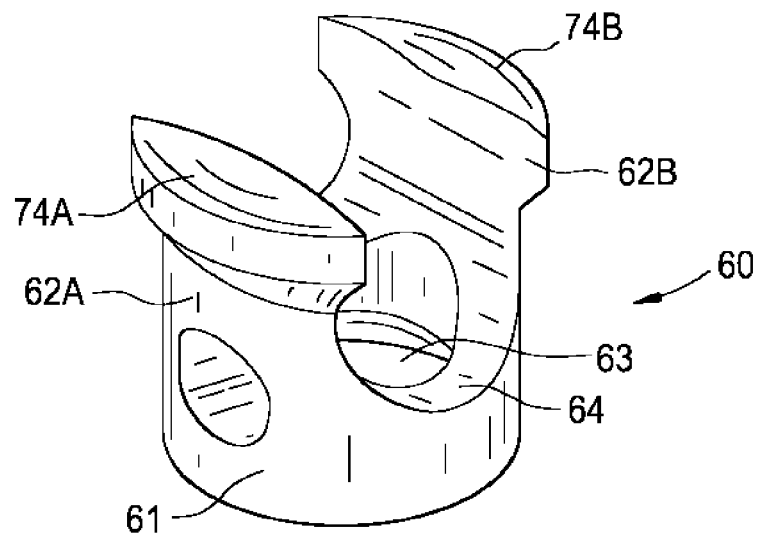
FIG. 4 is a perspective view of the compression member of the bone anchor assembly of FIG. 1.
Figure 5:
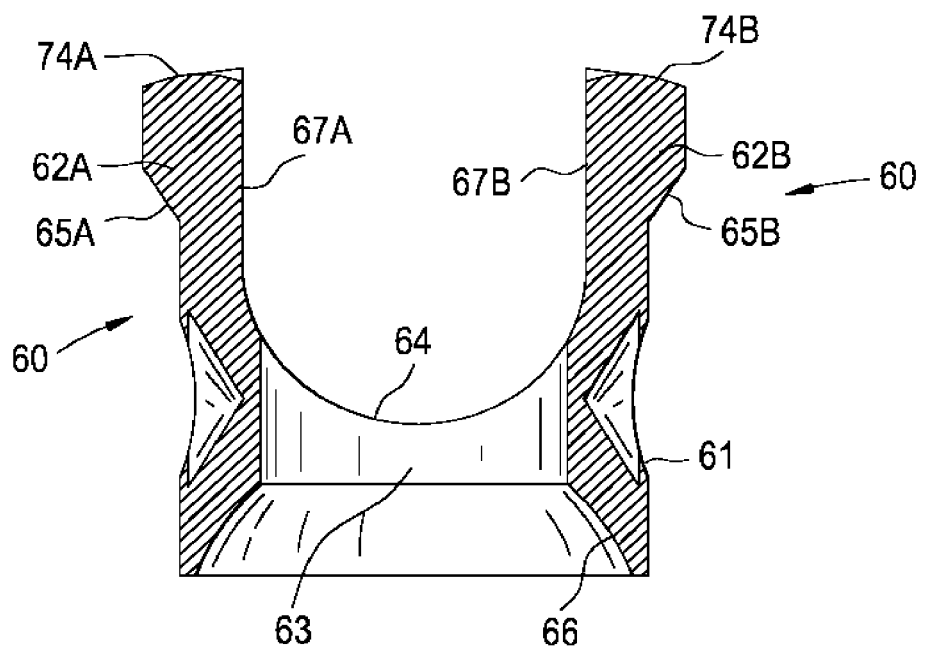
FIG. 5 is a cross sectional view of the compression member of the bone anchor assembly FIG. 1.
Figure 6:
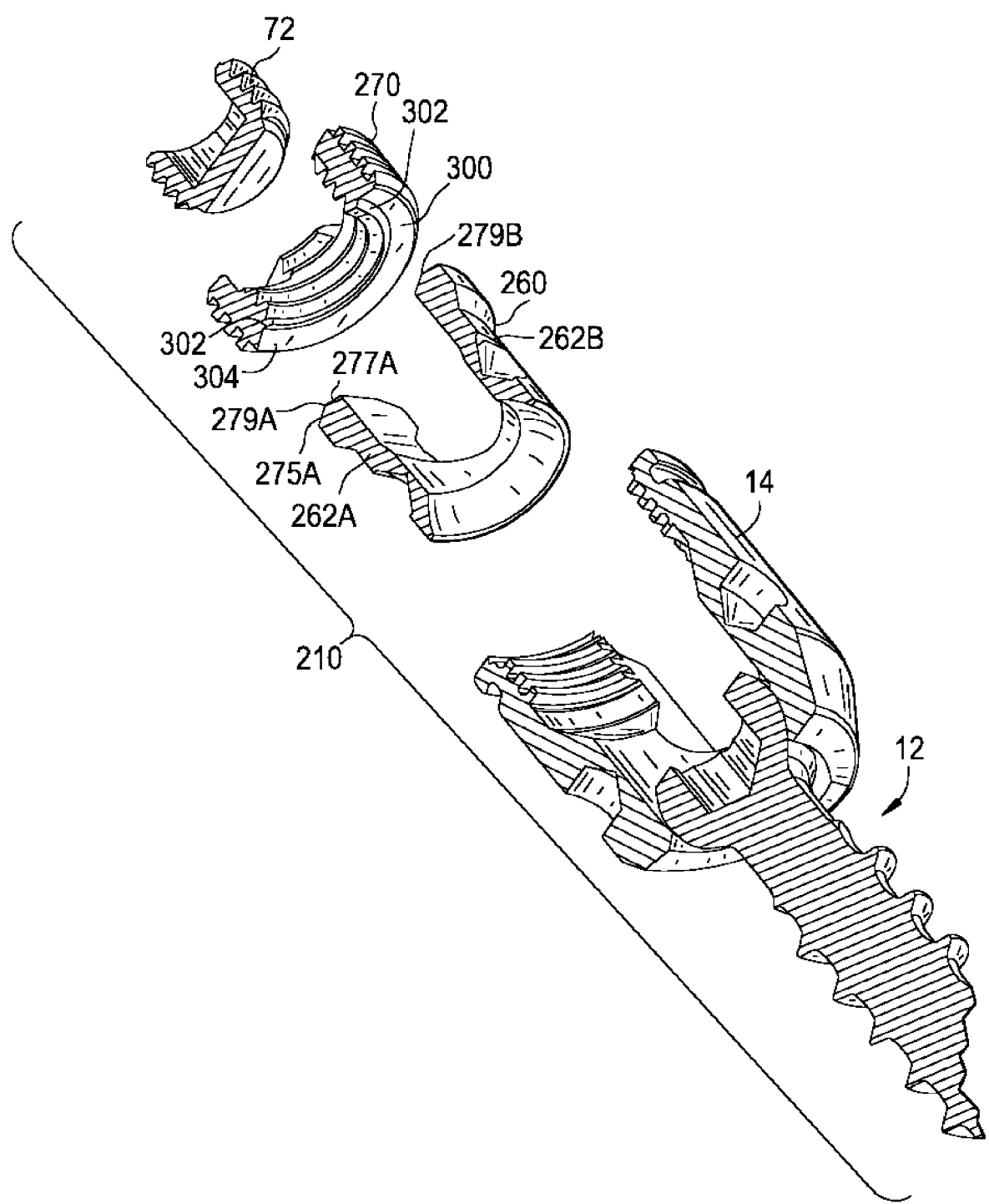
FIG. 6 is an exploded view in cross section of another exemplary embodiment of a bone anchor assembly.
Figure 7:
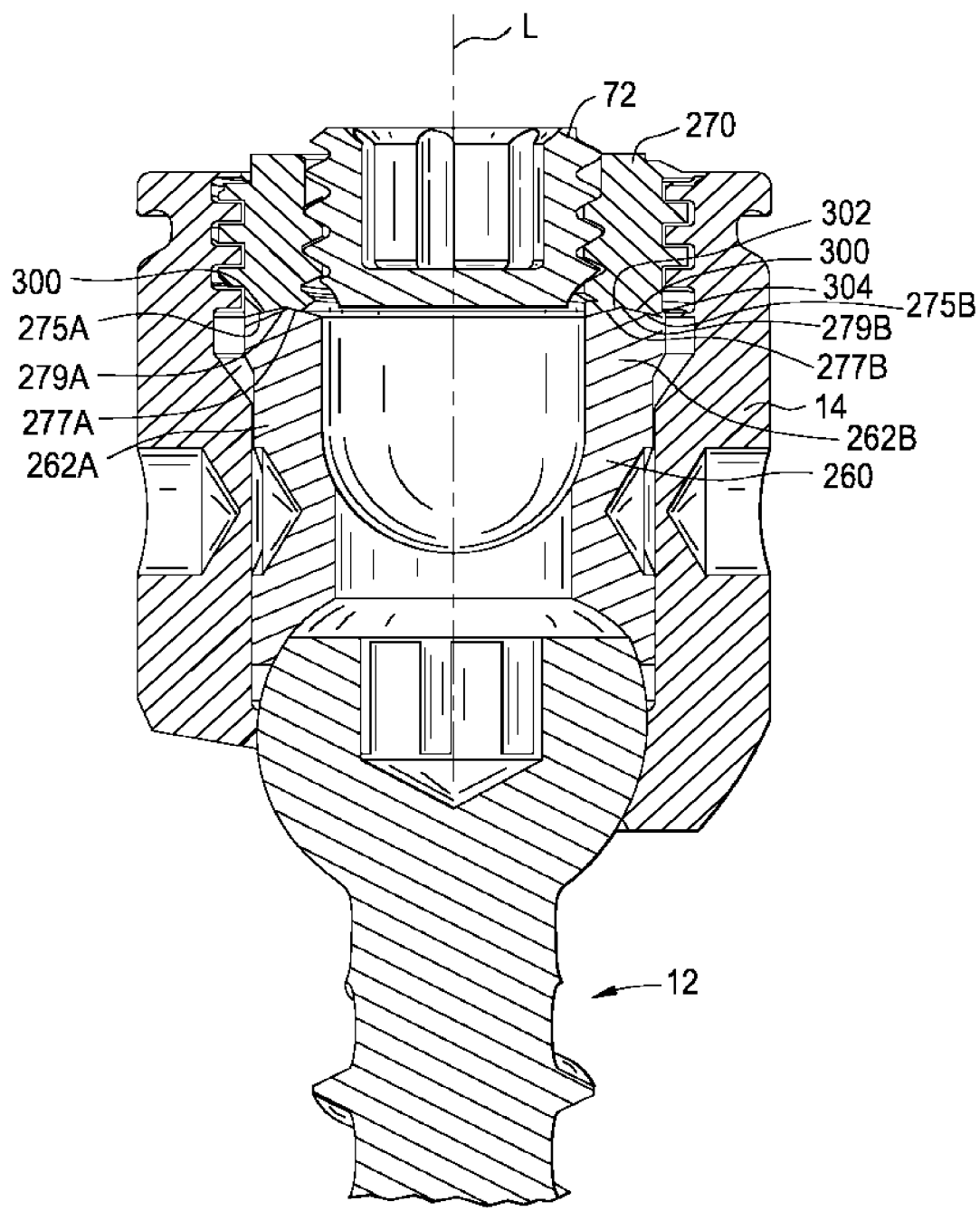
FIG. 7 is a side view in cross section of the bone anchor assembly of FIG. 6.
Figure 8:
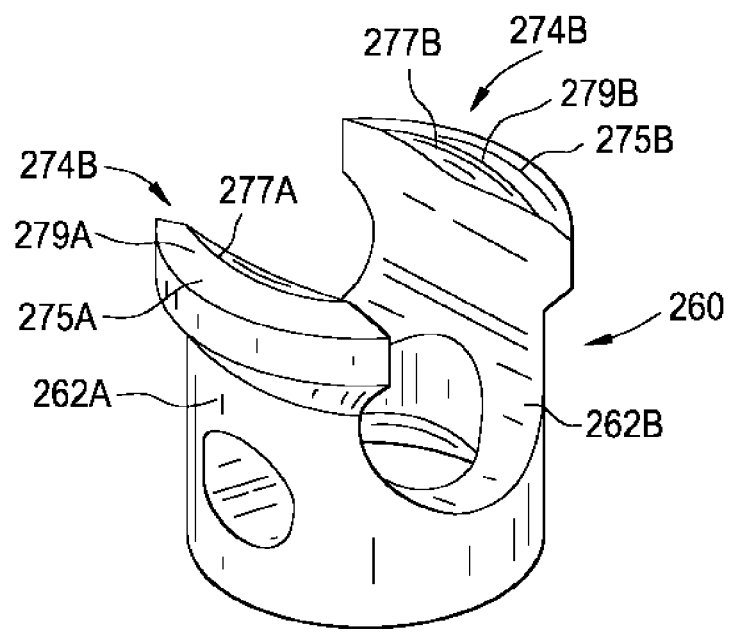
FIG. 8 is a perspective view of the compression member of FIG. 6.
Figure 9:
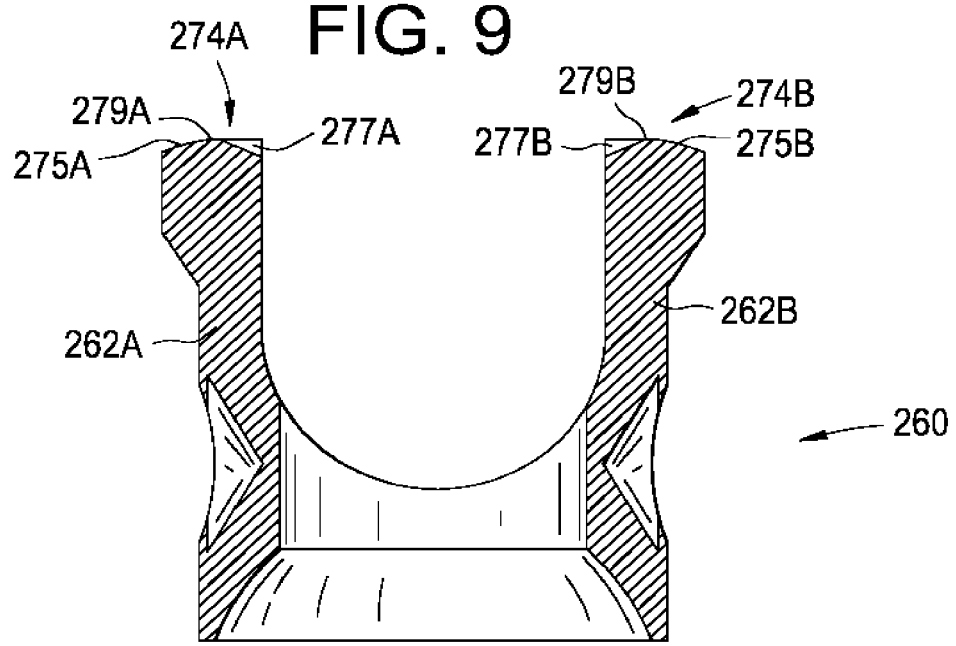
FIG. 9 is a side view in cross section of the compression member of FIG. 6.

The spinal fixation element, e.g., a spinal rod 22 in FIG. 3, contacts an intermediate element, e.g., a compression member 60, positioned within the central passage 37 of the receiver member 14 and interposed between the spinal rod 22 and the proximal head 18 of the bone anchor 12 to compress the distal outer surface 38 of the proximal head 18 into direct, fixed engagement with the distal inner surface of the receiver member 18. In the exemplary embodiment, the compression member 60 includes a pair of spaced compression member apart arms 62A and 62B defining a U-shaped seat 64 for receiving the spinal rod 22 and a distal surface 66 for engaging the proximal head 18 of the bone anchor 12, as illustrated in FIGS. 3-5. Each compression member arm 62A and 62B includes an outer wall 65A,B and an inner wall 67A,B and a proximal surface 74A, 74b of each compression member arm 62A, 62B connects the respective outer wall 65A,65B and the respective inner wall 67A, 67B. Each compression member arm 62A, 62B of the compression member 60 extends from a distal end 61 of the compression member 60 to a free end that terminates in a respective proximal surface 74A and 74B. The distal end of the compression member 60 is generally annular in shape and has a central opening 61 having a central longitudinal axis that is coincident with the central longitudinal axis L of the central passage 67 when the compression member 60 is positioned within the central passage 37 of the receiver member 14. The distal surface 66 surrounds the distal opening in the central passage 67 and is generally annular in shape when viewed from the bottom of the compression member 60.

The proximal end 26 of the receiving member 14 may be configured to receive a closure mechanism 16 positionable between and engaging the receiver member arms 28A and 28B of the receiver member 14 to capture a spinal fixation element, e.g., a spinal rod 22, within the receiver member 14, to fix the spinal rod 22 relative to the receiver member 14, and to fix the bone anchor 12 relative to the receiver member 14, as illustrated in FIG. 3. In certain exemplary embodiments, the closure mechanism 16 may be a single set screw having an outer thread for engaging an inner thread 42 provided on the receiver member arms 28A and 28B of the receiver member 14. In the exemplary embodiment, the closure mechanism 16 comprises an outer set screw 70 positionable between and engaging the receiver member arms 28A and 28B of the receiver member 14 and an inner set screw 72 positionable within the outer set screw 70. The outer set screw 70 is operable to act on the compression member 60 to fix the bone anchor 12 relative to the receiver member 14. The inner set screw 72 is operable to act on the spinal rod 22 to fix the spinal rod 22 relative to the receiver member 14. In this manner, the closure mechanism 16 permits the bone anchor 12 to be fixed relative to the receiver member 14 independently of the spinal rod 22 being fixed to the receiver member 14. In particular, the distal surface 100 of the outer set screw 70 can engage the proximal end surfaces 74A and 74B of the compression member arms 62A and 62B of the compression member 60 to force the distal surface 66 of the compression member 60 into contact with the proximal head 18 of bone anchor 12, which in turn forces the distal surface 38 of the proximal head 18 into the fixed engagement with the distal inner surface of the receiver member 14. The inner set screw 72 can engage the spinal rod 22 to force the spinal rod 22 into fixed engagement with the rod seat 64 of the compression member 60.

The outer set screw 70 of the exemplary closure mechanism 16 includes a first outer thread 76 for engaging the complementary inner thread 42 on the receiver member arms 28A and 28B of the receiver member 14. The thread form for the first outer thread 76 and the inner thread 42, including the number of threads, the pitch, major and minor diameter, and thread shape, may be selected to facilitate connection between the components and transfer of the desired axial tightening force. In the illustrated embodiment, for example, the first outer thread 76 and the inner thread 42 are square threads. Further exemplary thread forms are described in commonly-owned U.S. Patent Application Publication No. 2013-0096618, filed Oct. 9, 2012, which is incorporated herein by reference.

The outer set screw 70 may have a central passage 96 from a proximal surface 98 of the outer set screw 70 to a distal surface 100 of the outer set screw 74 for receiving the inner set screw 72. The central passage 96 may have an inner thread 102 for engaging a complementary outer thread 104 on the inner set screw 72. The thread form for the inner thread 102 and the outer thread 104, including the number of threads, the pitch, major and minor diameter, and thread shape, may be selected to facilitate connection between the components and transfer of the desired axial tightening force. In the illustrated embodiment, for example, the inner thread 102 and the outer thread 104 are M7×1 metric threads.

The proximal surface 98 of the outer set screw 70 may have one or more drive features to facilitate rotation and advancement of the outer set screw 74 relative to the receiver member 14. In the exemplary embodiment, the drive features are a plurality of cut-outs spaced-apart about the perimeter of the top surface 98. In the inner set screw 72 may include drive feature for receiving an instrument to rotate and advance the inner set screw 72 relative to the outer set screw 74. In the illustrated embodiment, for example, the inner set screw 72 includes a central passage 108 having a plurality of spaced apart, longitudinally oriented cut-outs for engaging complementary features on an instrument.

The exemplary bone anchor assembly 10 may be used with a spinal fixation element such as rigid spinal rod 22. The spinal rod 22 may be constructed from titanium, titanium alloys, stainless steel, cobalt chrome, PEEK, or other materials suitable for rigid fixation. Alternatively, the spinal fixation element may be a dynamic stabilization member that allows controlled mobility between the instrumented vertebrae.

As discussed above, engagement of the outer set screw 70 with the receiver member arms 28A and 28B results in the distal surface 100 of the outer set screw 70 engaging the proximal surface 74A and 74B of the compression member arms 62A and 62B. The outer set screw 70 thereby delivers a distal force to the compression member 60 that is transmitted through the compression member 60 to fix the bone anchor 12 relative to the receiver member 14. The proximal surfaces 74A and 74B of the compression member arms 62A and 62 can have a shape configured to restrict deformation of the compression member arms 62A and 62B, in particular, separation or splaying of the compression member arms 62A and 62B (i.e., movement of the arms away from each other) or movement of the compression member arms 62A and 62 towards each other, during or as a result of tightening, by primarily directing the distal force from the compression member in direction parallel to the central longitudinal axis L and inhibiting transmission of the distal force in a direction non-parallel to the central longitudinal axis L, particularly in a direction away from the central longitudinal axis L. The distal surface 66 of the outer set screw 70 can have a shape that is complementary to the shape of the proximal surfaces 74A and 74B of the compression member arms 62A and 62B. In the exemplary embodiment illustrated in FIGS. 1-5, the proximal surface 74A and 74B of each compression member arm 62 A and 62B is convex in shape and the distal surface 66 of the outer set screw 70 is concave in shape. In the exemplary embodiment, the convex proximal surfaces 74A and 74B have a single, constant radius from the respective outer surface 65A and 65B and the respective inner surface 67A and 67B and the concave distal surface 66 has a constant radius equal to the radius of the convex proximal surfaces 74A and 74B.

Figure 26:
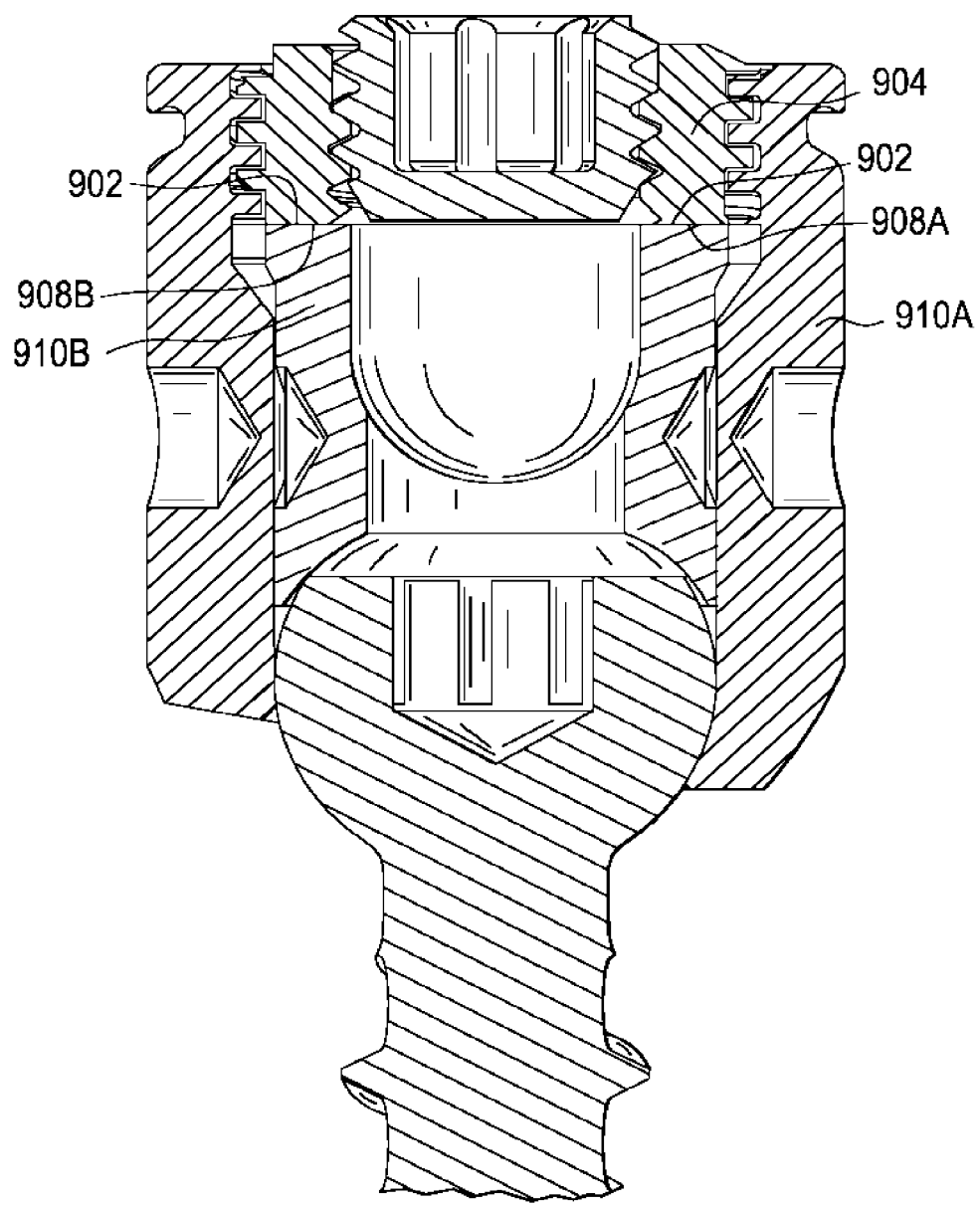
FIG. 26 is a side view in cross section of a prior art bone screw assembly.

In prior art bone anchor assembly designs, as illustrated in FIG. 26, the distal surface 902 of the outer set screw 904 and the proximal surfaces 908A and 908B of the compression member arms 910A and 910B are flat surfaces. The interface between the distal surface 902 and the proximal surfaces 908A and 908B fails to limit or minimize transmission of the axial tightening force in a non-axial direction and therefore fails to minimize or limit the deformation, in particular, the separation or splaying of the compression member arms 910A and 910B during axially tightening of the outer set screw 904. In contrast, the concave and convex interface of the exemplary embodiment illustrated in FIGS. 1-5, effectively restricts the deformation of the compression member 60 and, in particular, the movement of the compression member arms 62A and 62B relative each other (e.g., both towards and away from each other). By doing so, instances of the closure mechanism 16 loosening over time are reduced.

FIGS. 6-9 illustrate another exemplary bone anchor assembly 210 in which the proximal surfaces 274A and 274B of each compression member arm 262A and 262B of the compression member 260 has a peaked shape. Each peaked proximal surface 274A and 274B having a first angled surface 275A and 275B that intersects a second angled surface 277A and 277B at a peak 279A and 279B. In the exemplary embodiment, the distal surface 300 of the outer set screw 270 includes a third angled surface 302 that intersects an fourth angled surface 304 to define a V-shaped distal surface 300 complementary in shape to the peaked proximal surfaces 274A and 274B. For example, the angle of the first angled surface 275A and 275B relative to a central longitudinal axis of the compression member 210 (which is coincident with the central longitudinal axis L of the receiver member 14 when the compression member 260 is positioned within the central passage 37 of the receiver member 14) is equal to the angle of the third angled surface 302 relative to the central longitudinal axis of the outer set screw 270 and the angle of the second angled surface 277 A and 277B relative to the central longitudinal axis of the compression member 260 is equal to the angle of the fourth angled surface 304 relative to the central longitudinal axis of the outer set screw 270. The peaked interface between the proximal surfaces 274A and 274B of the compression member arms 262A and 262B and the distal surface 300 of the outer set screw, like the concave/convex interface described above, effectively restricts the deformation of the compression member 260 and, in particular, movement of the compression member arms 262A and 262B relative to each other.

Figure 10:
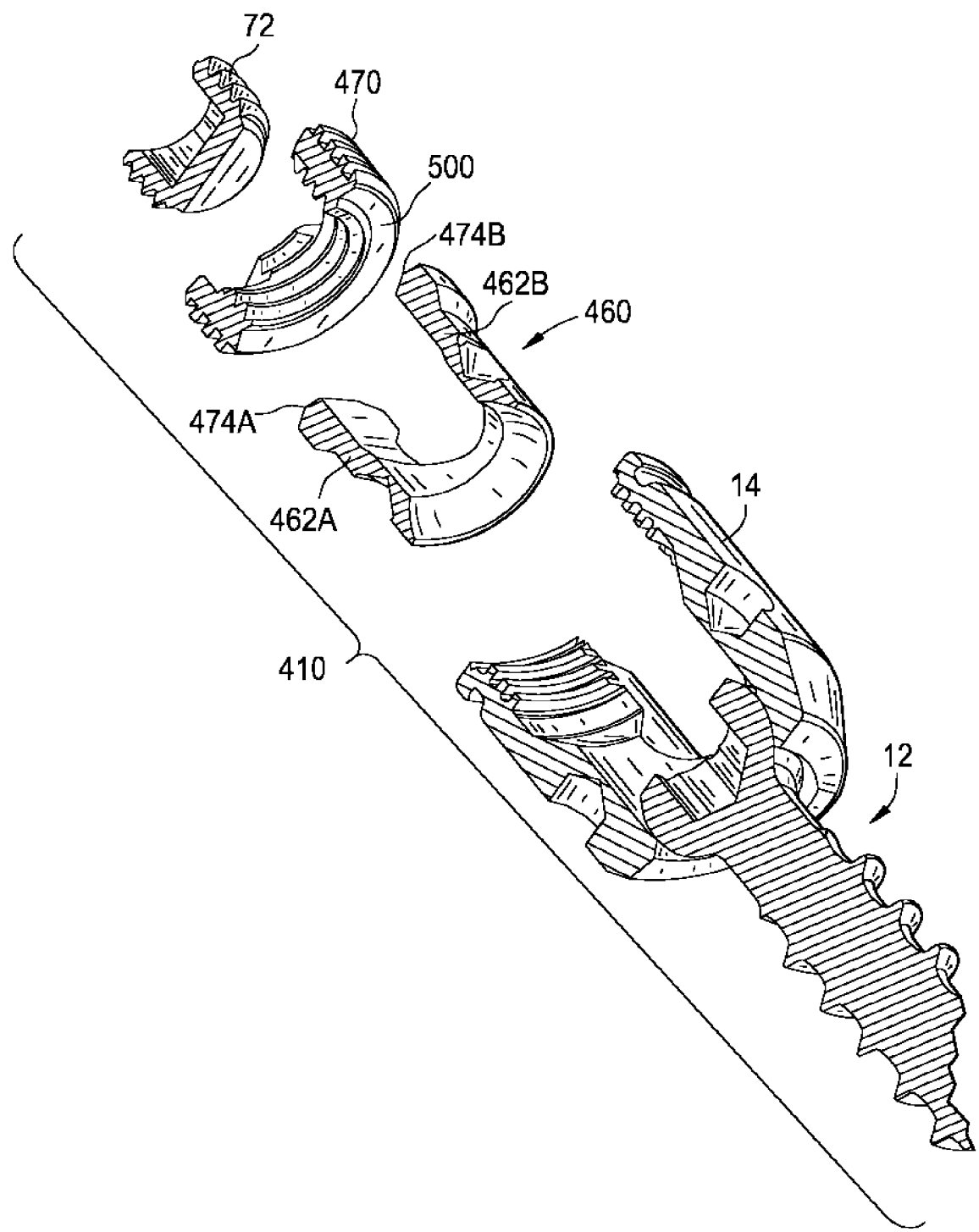
FIG. 10 is an exploded view in cross section of another exemplary embodiment of a bone anchor assembly.
Figure 11:
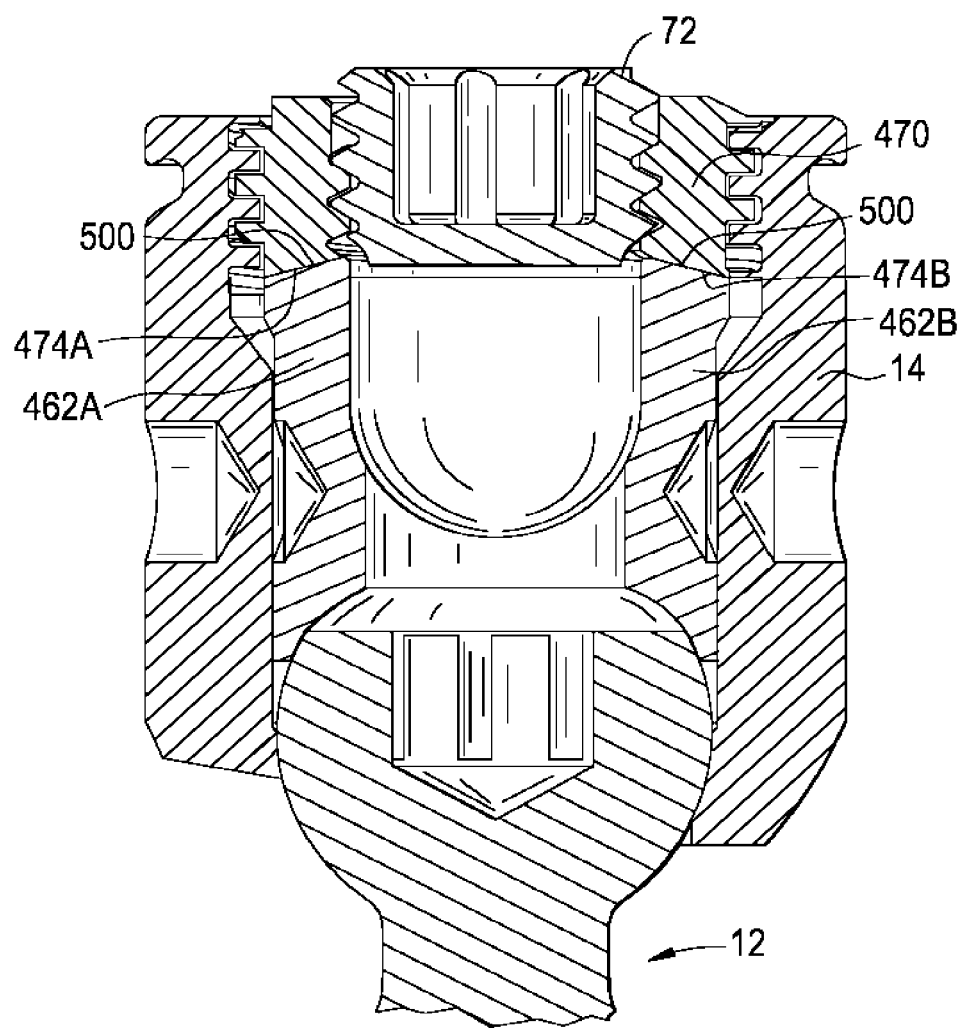
FIG. 11 is a side view in cross section of the bone anchor assembly of FIG. 6.
Figure 12:
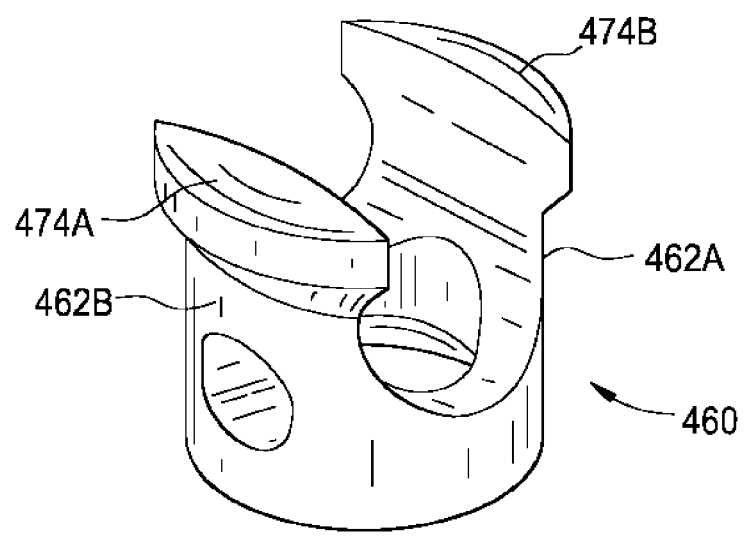
FIG. 12 is a perspective view of the compression member of FIG. 6.
Figure 13:
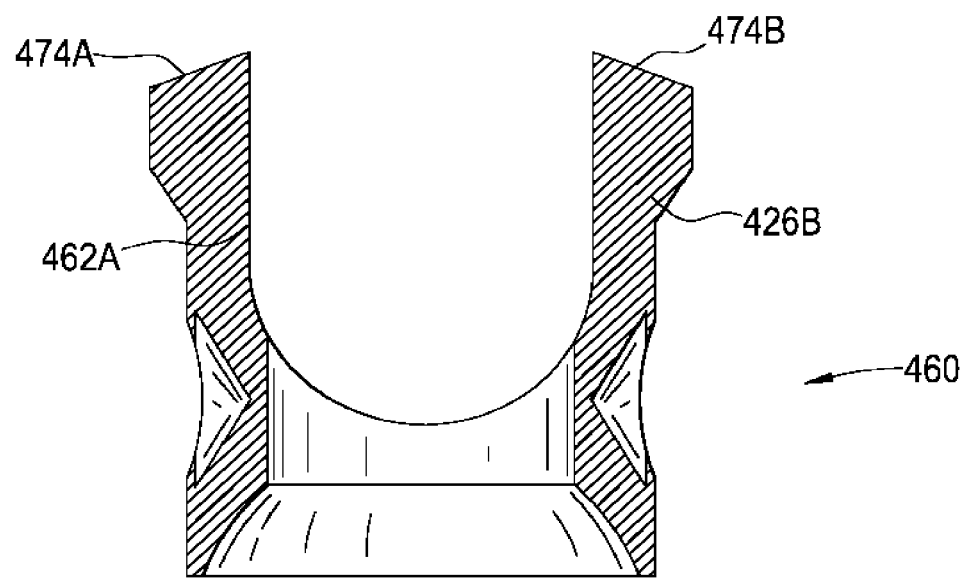
FIG. 13 is a side view in cross section of the compression member of FIG. 6.

FIGS. 10-12 illustrate another exemplary bone anchor assembly 410 in which the proximal surfaces 474A and 474B of each compression member arm 462A and 462B of the compression member 460 is angled from the respective outer wall 465A and 467B to the respective inner wall 467A and 467B. The distal surface 500 of the outer set screw 470 is conical in shape having an angle that is complementary to the angle of the angled proximal surfaces 474A and 474B. The peaked interface between the proximal surfaces 474A and 474B of the compression member arms 462A and 462B and the distal surface 506 of the outer set screw, like the concave/convex interface described above, effectively restricts the deformation of the compression member 460 and, in particular, movement of the compression member arms 462A and 462B relative to each other.

Figure 14:
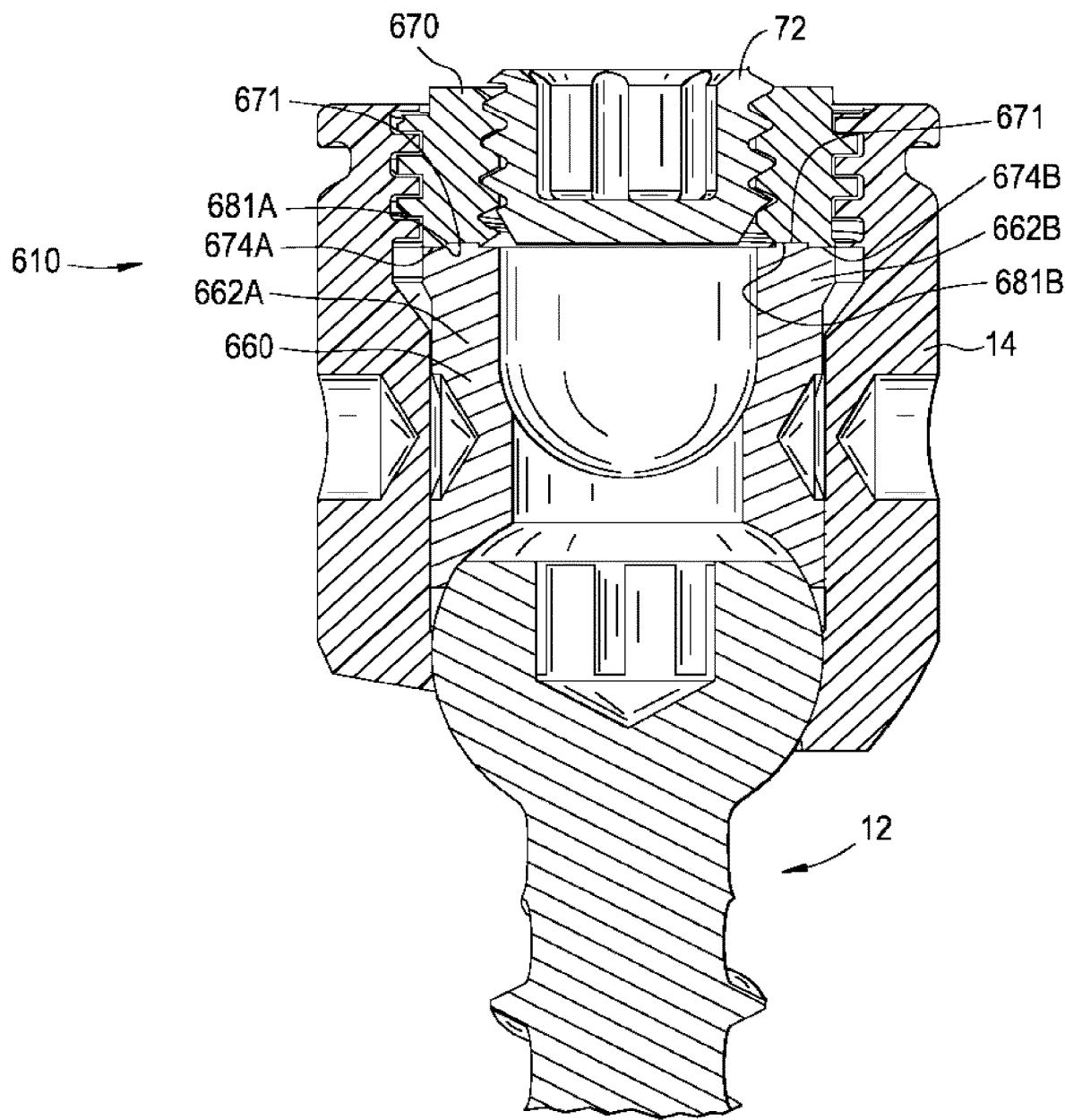
FIG. 14 is a side view in cross section of another exemplary embodiment of a bone anchor assembly.

FIG. 14 illustrates another exemplary bone anchor assembly 610 in which the proximal surfaces 674A and 674B of each compression member arm 662A and 662B of the compression member 660 is stepped in shape and has a centrally raised surface 681A and 681B. The distal surface of the outer set screw 670 includes an annular recess 671 that is complementary in size and shape to the centrally raised surface 681A and 681B proximal surfaces 674A and 674B. The centrally raised surface 681A and 681B proximal surfaces 674A and 674B seats within the annular recess 671 thereby restricting the deformation of the compression member 660 and, in particular, movement of the compression member arms 662A and 662B relative to each other.

FIGS. 15-25 illustrates other exemplary bone anchor assemblies in which the proximal surfaces or the compression member arms and the distal surface of the outer set screw are complementarily configured to restrict the deformation of the compression member and, in particular, movement of the compression member arms relative to each other.

Figure 15:
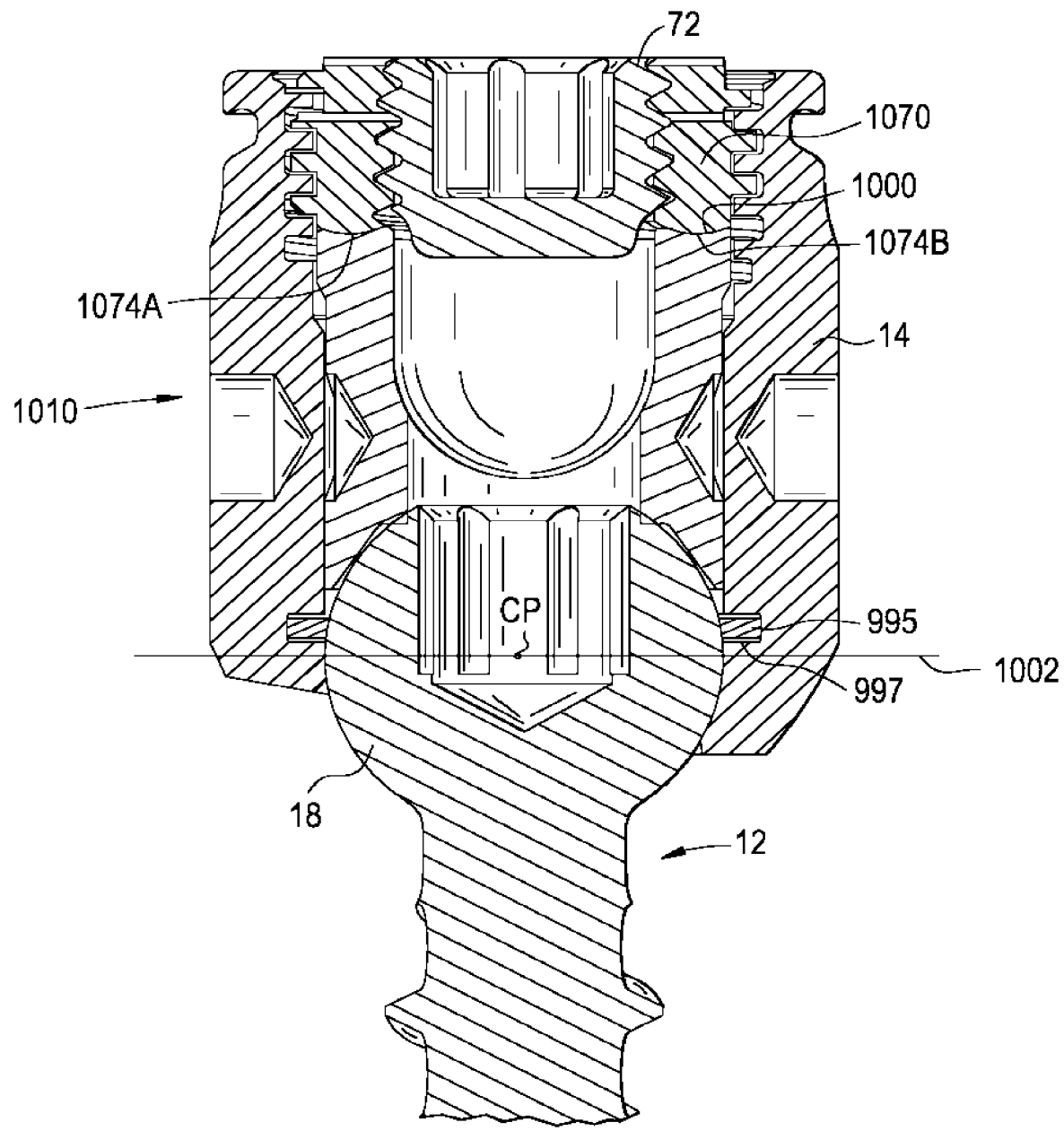
FIGS. 15-25 are side views in cross section of other exemplary embodiments of a bone anchor assembly.

In the exemplary bone anchor assembly 1010 of FIG. 15, the distal surface 1000 of the outer set screw 1070 is convex in shape and the proximal surfaces of 1074A and 1074B of the compression member arms are concave in shape. In the exemplary embodiment, the convex distal surface 1000 and the respective concave proximal surfaces 1074A and 1074B each have a constant radius that extends across the entire surface (when viewed in cross section as in FIG. 15) from the outer edge to the inner edge of the surface. In the exemplary embodiment, the radius of the convex distal surface 1000 and radius of the respective concave proximal surfaces 1074A and 1074B are equal. The exemplary bone anchor assembly 1010 further includes a drag member in the form of a split elastomeric ring 995 that is positioned within an annular groove 997 formed in the inner wall of the receiver member 14. The groove 997 and, thus the ring 995, is positioned within the receiver member 14 such that the ring 995 engages the proximal head 18 of the bone anchor 12 above the center point CP of the head 18 or above a line 1002 that intersects the center point CP of the head 18 and is oriented orthogonal to the longitudinal axis of receiver member 14 when the bone anchor 12 is in the neutral position, as illustrated in FIG. 15.

Figure 16:
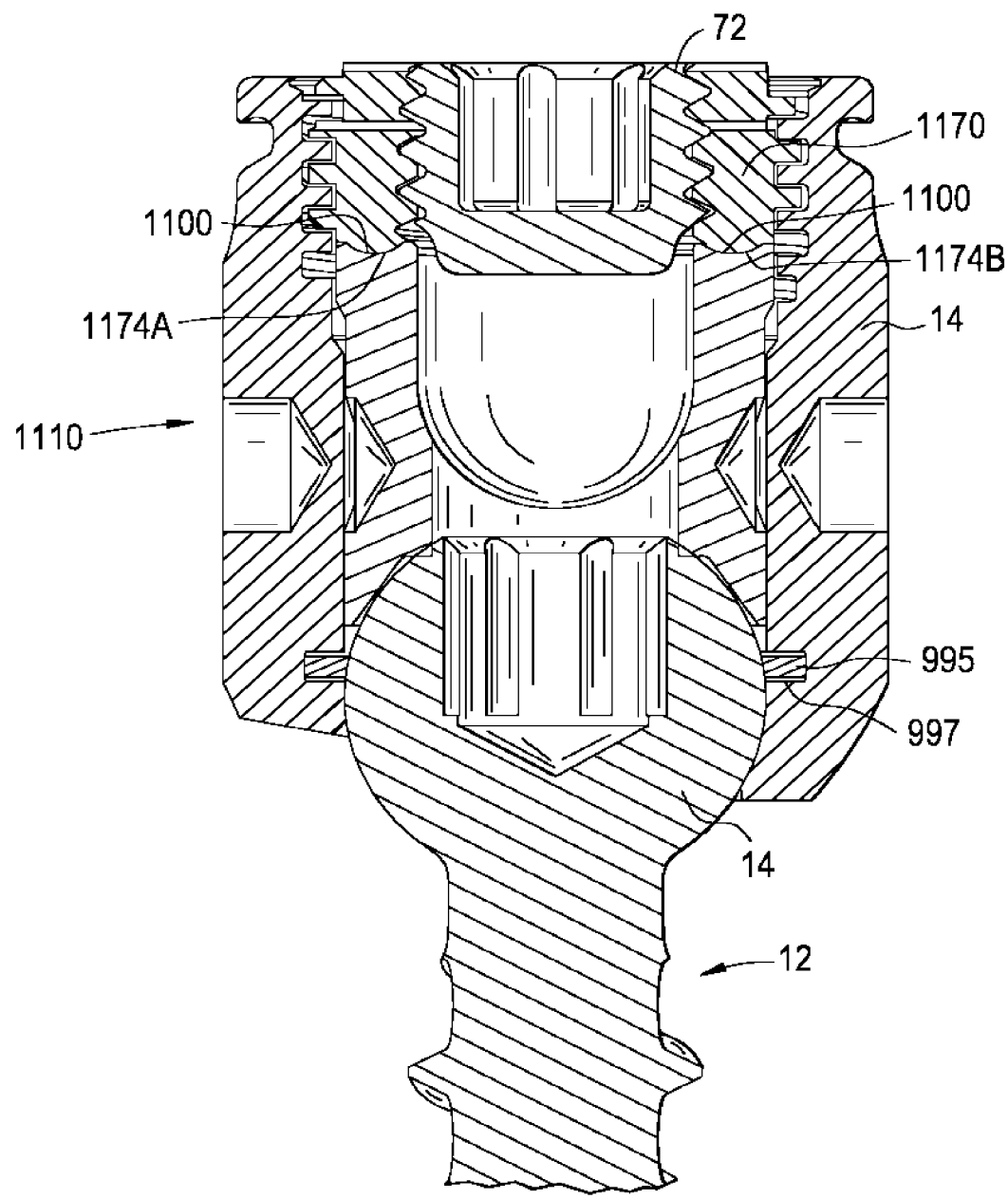

In the exemplary bone anchor assembly 1110 of FIG. 16, the distal surface 1100 of the outer set screw 1170 includes a projection that is convex in shape and the proximal surfaces of 1174A and 1174B of the compression member arms each include a complementary shaped concave recess in which the convex projection on the distal surface 1100 of the outer set screw can be seated.

Figure 17:
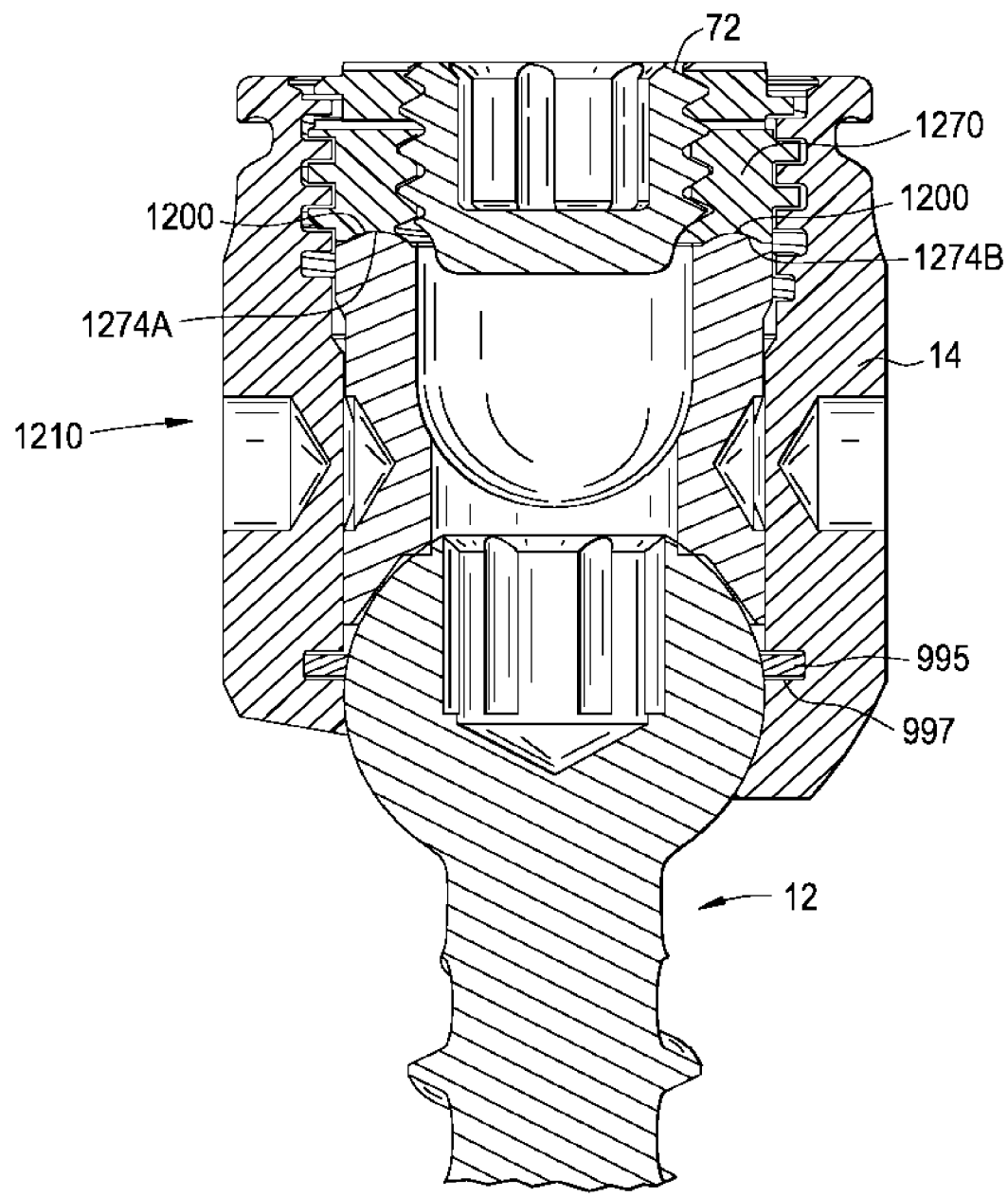

In the exemplary bone anchor assembly 1210 of FIG. 17, the proximal surfaces of 1274A and 1274B of the compression member arms each include a convex projection and the distal surface 1200 of the outer set screw 1270 includes a complementary shaped concave recess or groove in which the convex projections on the proximal surfaces 1274A and 1274B can be seated.

Figure 18:
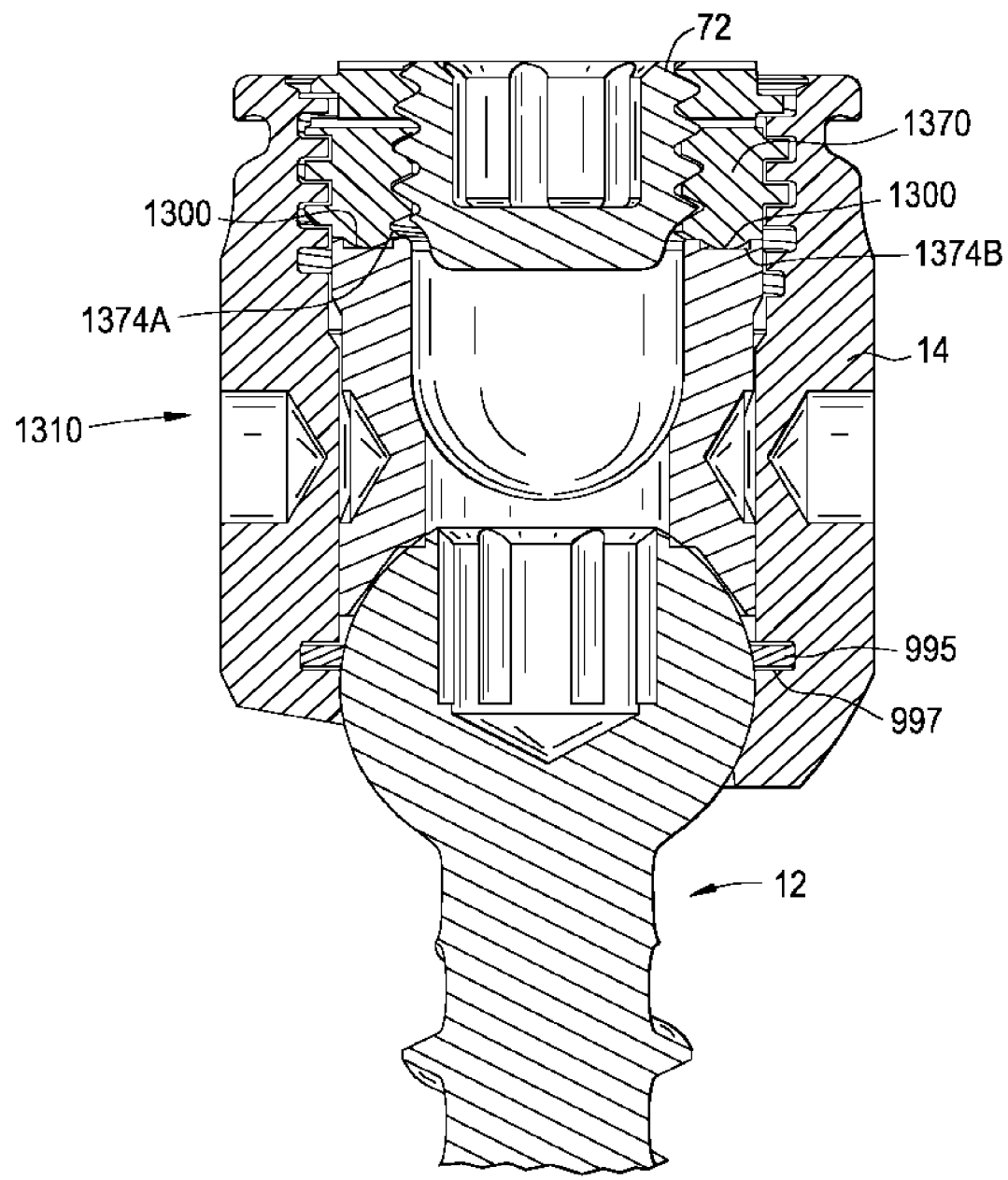

In the exemplary bone anchor assembly 1310 of FIG. 18, the distal surface 1300 of the outer set screw 1370 includes a projection that is convex in shape and the proximal surfaces 1374A and 1374B of the compression member arms each have a rectilinear shaped groove (when viewed in cross section as in FIG. 18) that receives the convex projection of the distal surface 1300 of the outer set screw 1370.

Figure 19:
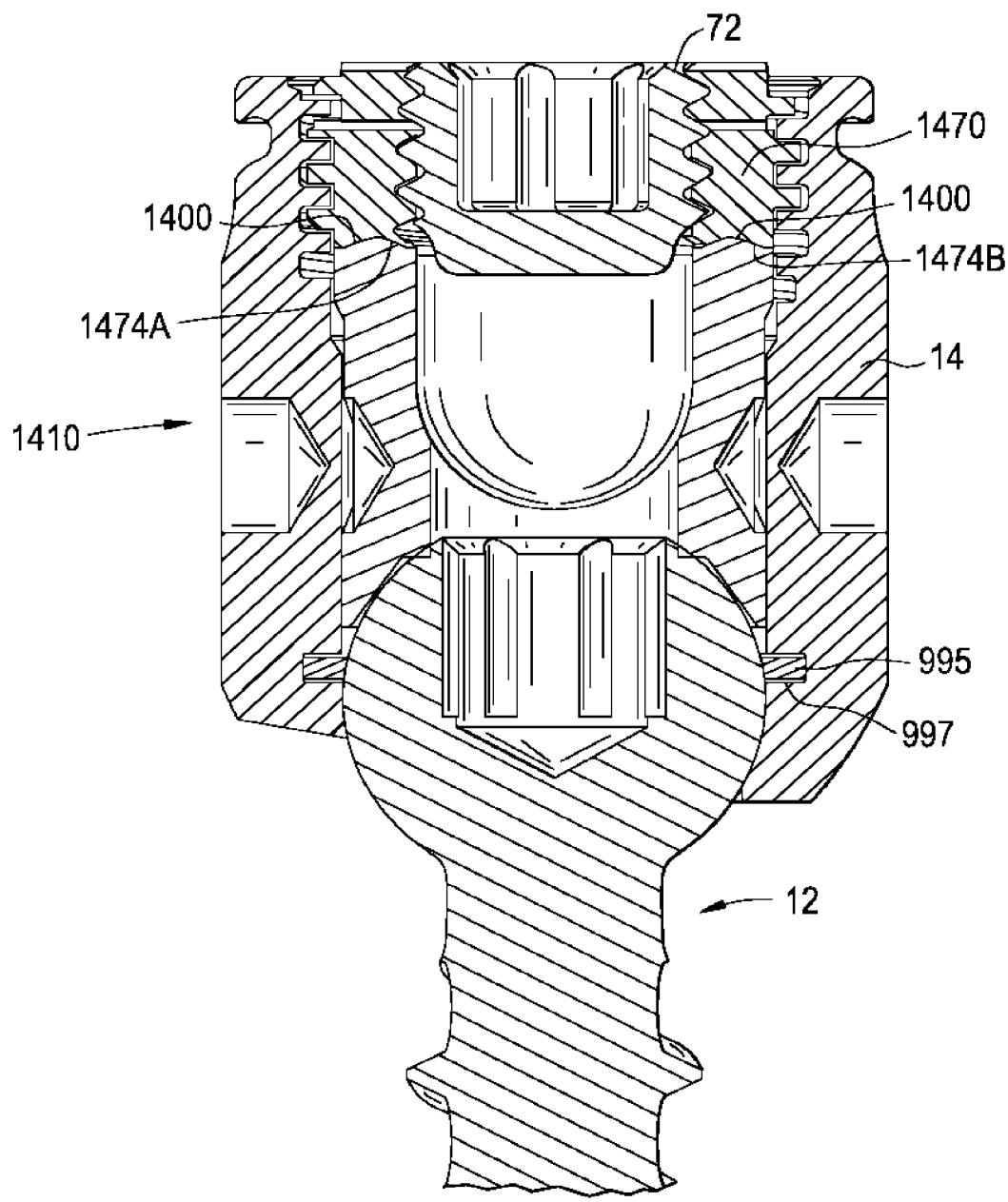

In the exemplary bone anchor assembly 1410 of FIG. 19, the proximal surfaces of 1474A and 1474B of the compression member arms each include a convex projection and the distal surface 1400 of the outer set screw 1470 includes a V-shaped recess or groove that receives the convex projections on the proximal surfaces of 1474A and 1474B.

Figure 20:
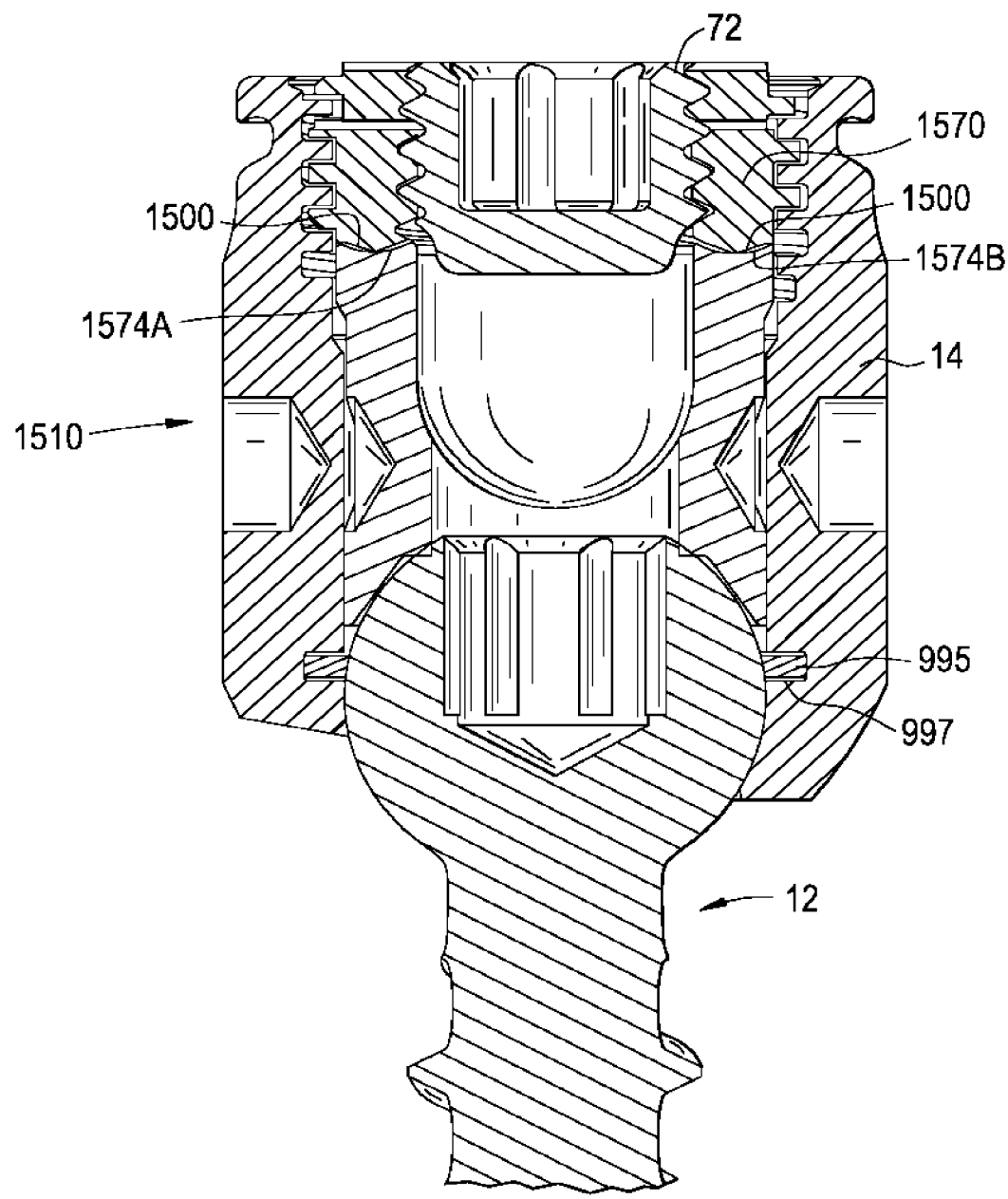

In the exemplary bone anchor assembly 1510 of FIG. 20, the distal surface 1500 of the outer set screw 1570 is peaked having a first angled surface that intersects a second angled surface at a peak and the proximal surfaces of 1574A and 1574B of the compression member arms are concave in shape.

Figure 21:
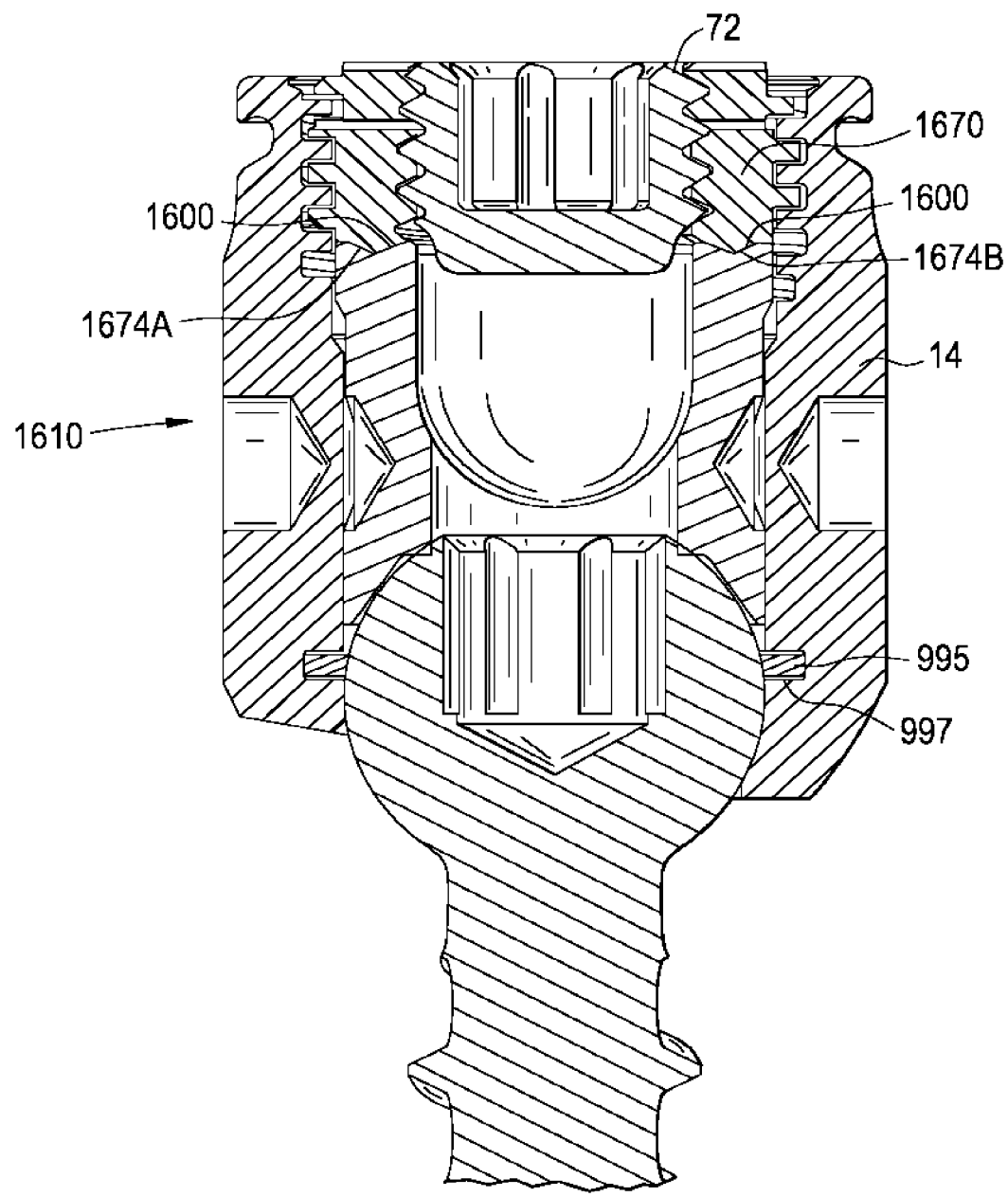

In the exemplary bone anchor assembly 1610 of FIG. 21, the distal surface 1600 of the outer set screw 1670 includes a projection that is convex in shape and the proximal surfaces 1674A and 1674B of the compression member arms each have a V-shaped groove (when viewed in cross section as in FIG. 21) that receives the convex projection of the distal surface 1600 of the outer set screw 1670.

Figure 22:
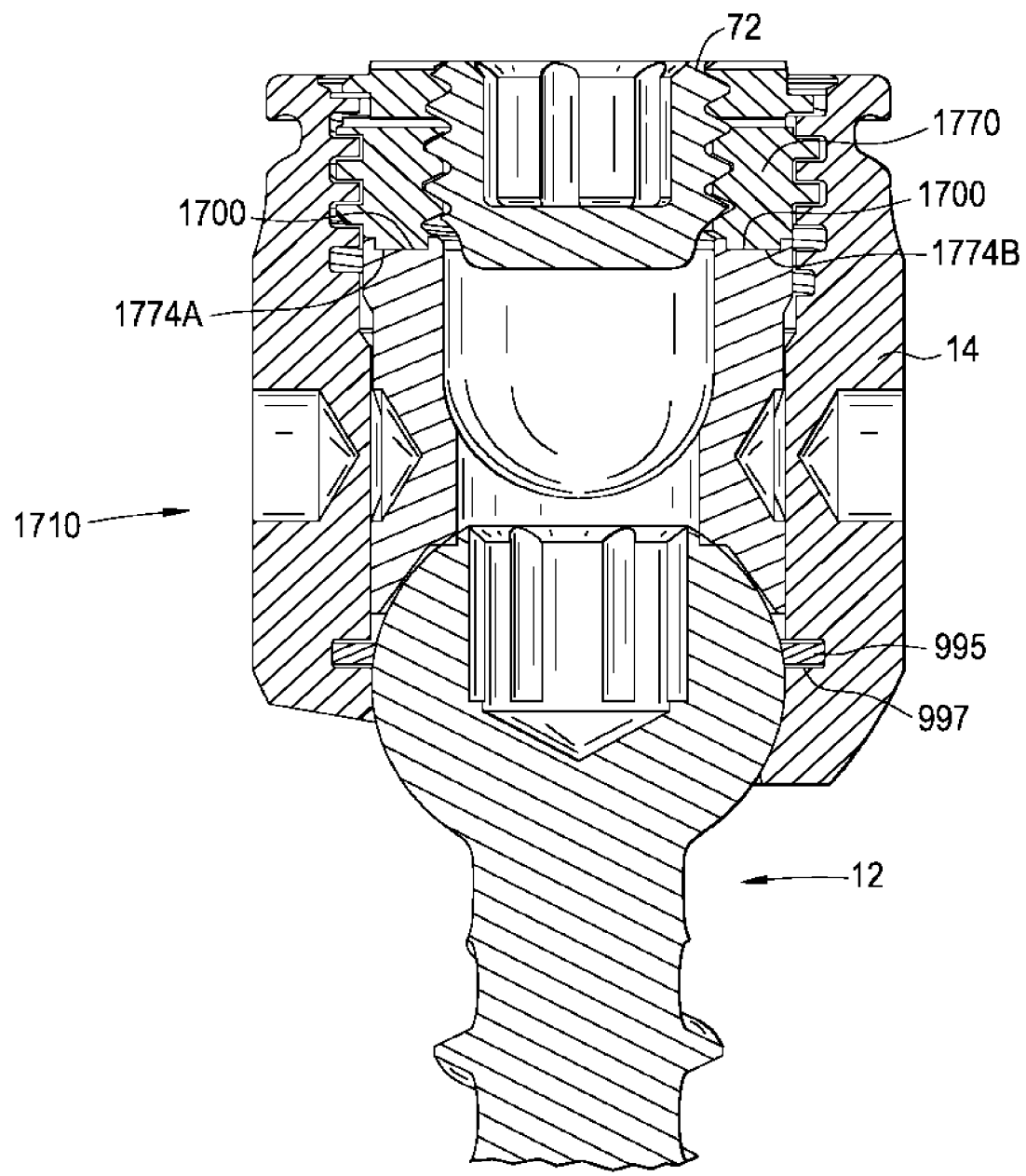

In the exemplary bone anchor assembly 1710 of FIG. 22, the distal surface 1700 of the outer set screw 1770 includes a projection that is rectilinear in shape and the proximal surfaces 1774A and 1774B of the compression member arms each have a complementary shaped rectilinear groove (when viewed in cross section as in FIG. 22) that receives the rectilinear projection of the distal surface 1700 of the outer set screw 1770.

Figure 23:
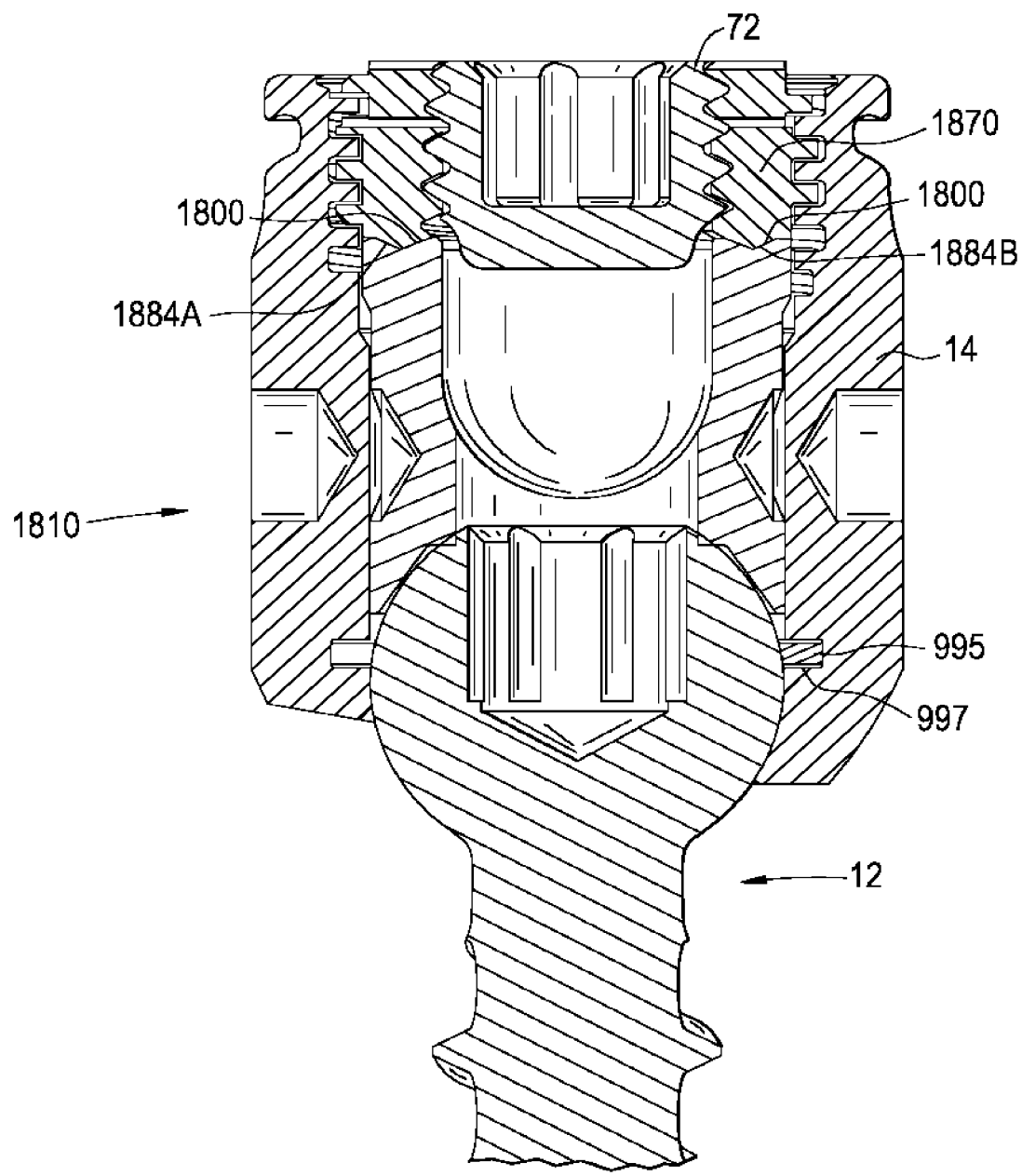

In the exemplary bone anchor assembly 1810 of FIG. 23, the distal surface 1800 of the outer set screw 1870 has a peaked projection that has a first angled surface that intersects a second angled surface at a peak and the proximal surfaces 1874A and 1874B of the compression member arms each have a complementary shaped V-shaped groove (when viewed in cross section as in FIG. 23) that receives the peaked shaped projection of the distal surface 1800 of the outer set screw 1870.

Figure 24:
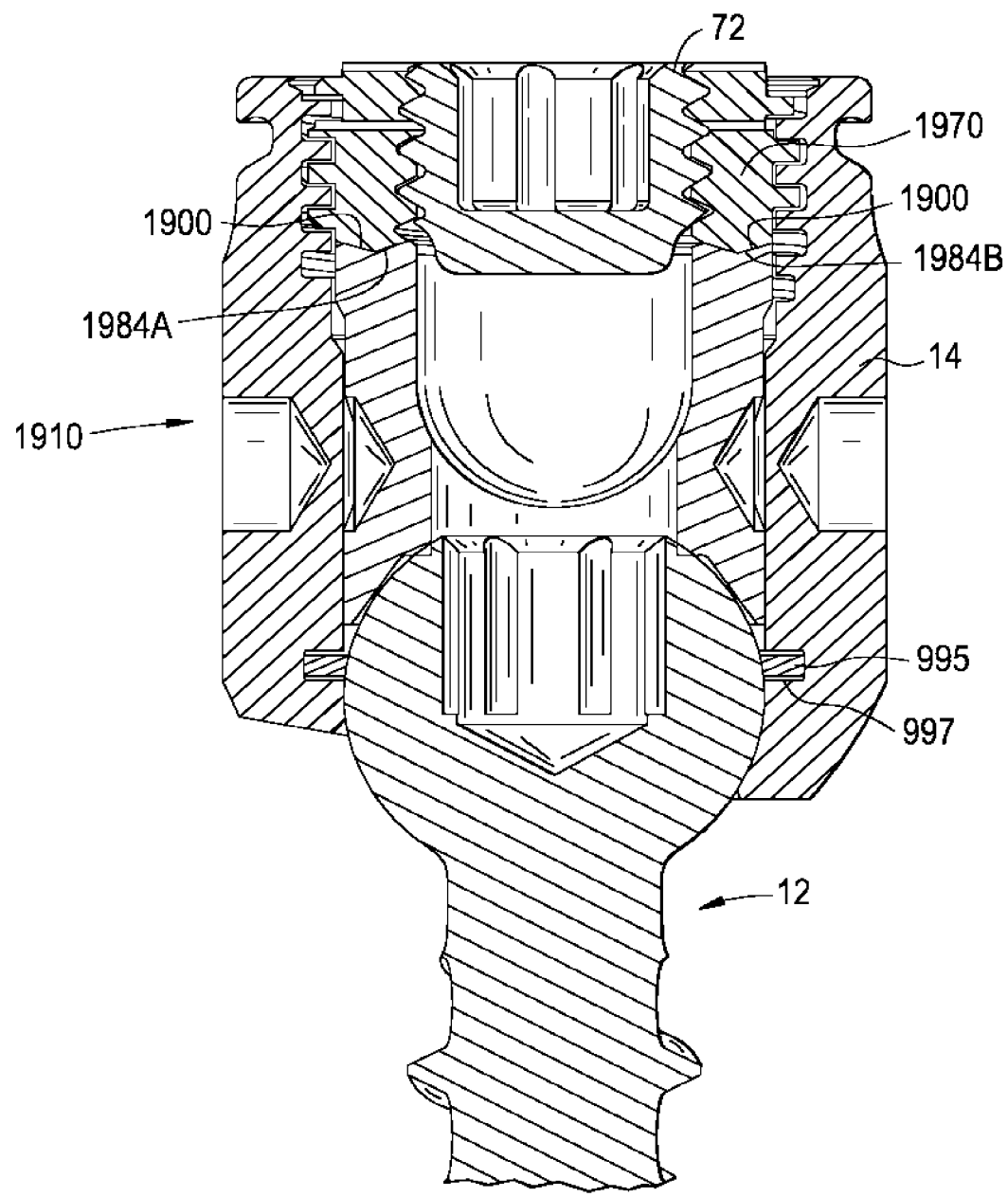

In the exemplary bone anchor assembly 1910 of FIG. 24, the distal surface 1900 of the outer set screw 1970 is peaked having a first angled surface that intersects a second angled surface at a peak and the proximal surfaces 1974A and 1974B of the compression member arms are V-shaped (when viewed in cross section as in FIG. 24).

Figure 25:
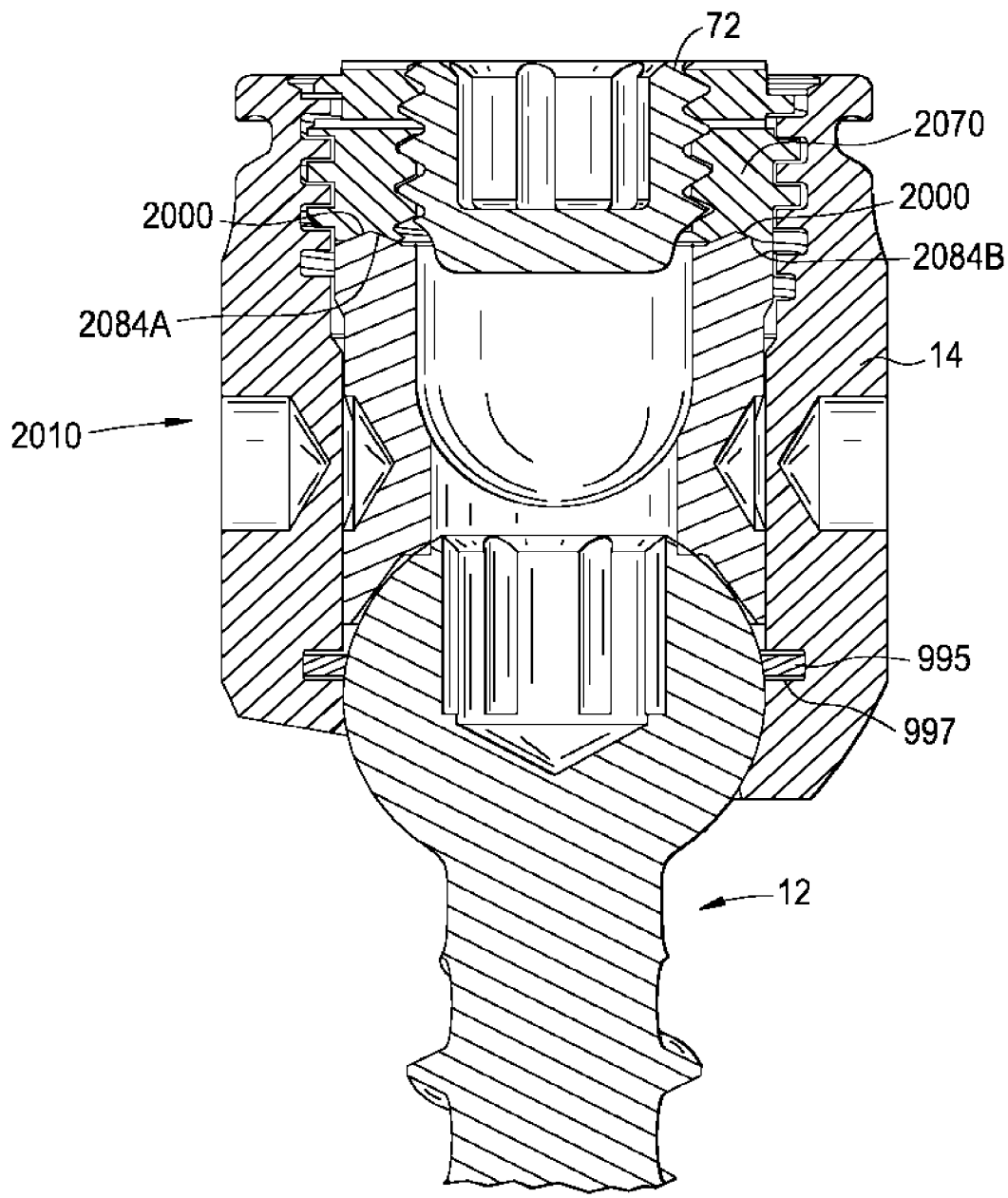

In the exemplary bone anchor assembly 2010 of FIG. 25, the proximal surfaces 2084A and 2084B of the compression member arms each have a peaked projection that has a first angled surface that intersects a second angled surface at a peak and the distal surface 2000 of the outer set screw 2070 has a complementary shaped V-shaped groove (when viewed in cross section as in FIG. 25) that receives the peaked shaped projections of the proximal surfaces 2084A and 2084B.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A bone anchor assembly comprising:
   a bone anchor having a proximal head and a distal shaft configured to engage bone,
   a receiver member for receiving a spinal fixation element to be coupled to the bone anchor, the receiver member having
      a proximal end having a pair of spaced apart receiver member arms defining a recess therebetween, the receiver member arms including an inner thread, a distal end having a distal end surface defining an opening through which at least a portion of the bone anchor extends, and a central passage extending between the proximal end and the distal end, the central passage communicating with the opening in the distal end surface, the central passage having a central longitudinal axis extending between the proximal end and the distal end, a compression member positioned within the receiver member, the compression member having a proximal end and a distal end, the proximal end of the compression member having a pair of spaced apart compression member arms defining a U-shaped seat for receiving the rod, each compression member arm having a proximal surface, each compression member arm including an outer wall and an inner wall, the proximal surface of the compression member arm connecting the outer wall and the inner wall, the distal end of the compression member having a distal surface engageable with the proximal head of the bone anchor, an outer set screw positionable between and engaging the receiver member arms, the outer set screw including a first outer thread for engaging the inner thread, the outer set screw having a distal surface engageable with the proximal surface of the compression member arms, the outer set screw having a set screw central passage from a top surface of the outer set screw to a bottom surface of the outer set screw, the set screw central passage having a second internal thread, and an inner set screw positionable within the set screw central passage, the inner set screw having a second outer thread for engaging the second inner thread, the inner set screw operable to act on the spinal rod to fix the spinal rod relative to the receiver member;

wherein engagement of the outer set screw with the receiver member arms results in the distal surface of the outer set screw engaging the proximal surface of the compression member arms and the outer set screw thereby delivering a distal force to the compression member to fix the bone anchor relative to the receiver member, the proximal surface of each of the compression member arms defining a recess to restrict relative movement of the compression member arms both towards and away from each other and the distal surface of the outer set screw having a projection sized and shaped to be seated in the recesses of the proximal surfaces.

2. The bone anchor assembly of claim 1, wherein the recess of the proximal surface of each compression member arm is concave in shape.

3. The bone anchor assembly of claim 2, wherein each concave recess has a constant radius.

4. The bone anchor assembly of claim 2, wherein the projection of the distal surface of the outer set screw is convex in shape.

5. The bone anchor assembly of claim 1, wherein each recess of the proximal surface has a constant radius and the projection of the distal surface has a constant radius equal to the radius of the recesses of the proximal surfaces.

6. The bone anchor assembly of claim 1, wherein the recess of the proximal surface of each compression member arm defines a rectilinear shaped groove.

7. The bone anchor assembly of claim 1, wherein the projection of the distal surface of the outer set screw is peaked, each peaked surface having a first angled surface that intersects a second angled surface at a peak.

8. The bone anchor assembly of claim 7, wherein the recess of the proximal surface of each compression member arm includes a third angled surface that intersects a fourth angled surface to define a V-shaped surface, and wherein the angle of the first angled surface relative to the central longitudinal axis is equal to the angle of the third angled surface relative to the central longitudinal axis and the angle of the second angled surface relative to the central longitudinal axis is equal to the angle of the fourth angled surface relative to the central longitudinal axis.

9. The bone anchor assembly of claim 1, wherein the bone anchor is movable relative to the receiver member.

10. The bone anchor assembly of claim 9, wherein the bone anchor has a first angular range of motion relative to the receiver member in at least a first direction relative to a central longitudinal axis and has a second angular range of motion relative to the receiver member in at least a second direction relative to the central longitudinal axis, the second angular range of motion being greater than the first angular range of motion.

11. The bone anchor assembly of claim 1, wherein the proximal end of the receiver member includes a proximal end surface that defines a first plane and wherein the distal end surface defines a second plane, the first plane and second plane intersecting one another.

12. A bone anchor assembly comprising:

a bone anchor having a proximal head and a distal shaft configured to engage bone, a receiver member for receiving a spinal fixation element to be coupled to the bone anchor, the receiver member having a proximal end having a proximal end surface and a pair of spaced apart receiver member arms defining a recess therebetween for receiving a spinal rod, the arms including a first inner thread, the proximal end surface defining a first plane, a distal end having a distal end surface defining an opening through which at least a portion of the bone anchor extends, the bone anchor being movable relative to the receiver member, the distal end surface defining a second plane, the first plane and the second plane intersecting one another, a compression member positioned within the receiver member, the compression member having a proximal end and a distal end, the proximal end of the compression member having a pair of spaced apart compression member arms defining a U-shaped seat for receiving the rod, each compression member arm including an outer wall, an inner wall and a proximal surface connecting the outer wall and the inner wall, the distal end of the compression member having a distal surface engageable with the proximal head of the bone anchor, an outer set screw positionable between and engaging the receiver member arms, the outer set screw including a first outer thread for engaging the first inner thread, the outer set screw having a distal surface engageable with the proximal surface of the compression member arms, the outer set screw having a set screw central passage from a top surface of the outer set screw to a bottom surface of the outer set screw, the set screw central passage having a second internal thread, and an inner set screw positionable within the set screw central passage, the inner set screw having a second outer thread for engaging the second inner thread, the inner set screw operable to act on the spinal rod to fix the spinal rod relative to the receiver member;

wherein engagement of the outer set screw with the receiver member arms results in the distal surface of the outer set screw engaging the proximal surface of the compression member arms and the outer set screw thereby delivering a distal force to the compression member to fix the bone anchor relative to the receiver member, the proximal surface of each of the compression member arms defining a recess to restrict relative motion of the compression member arms both towards and away from each other, the distal surface of the outer set screw having a projection sized and shaped to be seated in the recesses of the proximal surfaces.

13. The bone anchor assembly of claim 12, wherein the recess of the proximal surface of each compression member arm is concave in shape.

14. The bone anchor assembly of claim 13, wherein each proximal surface has a constant radius.

15. The bone anchor assembly of claim 13, wherein the projection of the distal surface of the outer set screw is convex in shape.

16. The bone anchor assembly of claim 15, wherein each concave recess has a constant radius and the convex projection of the distal surface has a constant radius equal to the radius of the concave proximal surfaces.

17. The bone anchor assembly of claim 12, wherein the recess of the proximal surface of each compression member arm defines a rectilinear shaped groove.

18. The bone anchor assembly of claim 12, wherein the distal surface of the outer set screw is peaked, each peaked surface having a first angled surface that intersects a second angled surface at a peak.

19. The bone anchor assembly of claim 18, wherein the recess of the proximal surface of each compression member arm includes a third angled surface that intersects a fourth angled surface to define a V-shaped surface, and wherein the angle of the first surface relative to the central longitudinal axis is equal to the angle of the third angled surface relative to the central longitudinal axis and the angle of the second surface relative to the central longitudinal axis is equal to the angle of the fourth angled surface relative to the central longitudinal axis.

* * * * *